US006610350B2

United States Patent
Suzuki et al.

(10) Patent No.: US 6,610,350 B2
(45) Date of Patent: Aug. 26, 2003

(54) METHOD OF MODIFYING OPHTHALMIC LENS SURFACE BY PLASMA GENERATED AT ATMOSPHERIC PRESSURE

(75) Inventors: Hiroaki Suzuki, Kasugai (JP); Yuuji Gotou, Kasugai (JP); Kazuhiko Nakada, Kasugai (JP)

(73) Assignee: Menicon Co., Ltd., Nagoya (JP)

( * ) Notice: Subject to any disclaimer, the term of this patent is extended or adjusted under 35 U.S.C. 154(b) by 0 days.

(21) Appl. No.: 09/968,222

(22) Filed: Oct. 1, 2001

(65) Prior Publication Data

US 2002/0064597 A1 May 30, 2002

(30) Foreign Application Priority Data

Oct. 5, 2000 (JP) ........................ 2000-306155
Aug. 7, 2001 (JP) ........................ 2001-239599

(51) Int. Cl.[7] ............................ A61L 27/00; B05D 3/04; B05D 5/00; B05D 1/02
(52) U.S. Cl. ................ 427/2.24; 427/2.1; 427/2.31; 427/162; 427/164; 427/421; 427/561; 427/562; 427/569; 427/580; 427/533; 427/535; 427/536
(58) Field of Search ................. 427/2.1, 2.24, 427/2.31, 162, 164, 421, 561, 562, 569, 580, 533, 535, 536

(56) References Cited

U.S. PATENT DOCUMENTS 4,859,908 A * 8/1989 Yoshida et al. ......... 118/723 R
5,466,424 A * 11/1995 Kusano et al. ......... 422/186.05
6,017,396 A * 1/2000 Okamoto ................ 118/719
6,202,292 B1 * 3/2001 Farnworth et al. ......... 269/21

FOREIGN PATENT DOCUMENTS

| EP | 0 758 687 A1 | 2/1997 | |
|----|----|----|----|
| JP | A-50-20652 | 3/1975 | |
| JP | A-55-151618 | 11/1980 | |
| JP | A-62-35326 | 3/1987 | |
| JP | B-1-43697 | 12/1989 | |
| JP | A-3-220519 | 9/1991 | |
| JP | A-4-89309 | 8/1992 | |
| JP | 05295143 A | * 11/1993 | ............ C08J/7/16 |
| JP | A-5-337957 | 12/1993 | |
| JP | A-6-208090 | 7/1994 | |
| JP | A-6-82923 | 11/1994 | |
| JP | A-8-456920 | 6/1996 | |
| JP | B2-2846343 | 10/1998 | |
| JP | A-10-315252 | 12/1998 | |
| JP | A-2000-266903 | 9/2000 | |
| WO | 99/57178 | 11/1999 | |

* cited by examiner

Primary Examiner—Shrive P. Beck
Assistant Examiner—Jennifer Kolb Michener
(74) Attorney, Agent, or Firm—Burr & Brown

(57) ABSTRACT

A method of modifying a surface of an ophthalmic lens, includes the steps of: generating plasma at an atmospheric pressure between electrodes of a plasma generating device; and blowing the plasma from the plasma generating device by introducing a gas between the electrodes. The ophthalmic lens, which is located outside the plasma generating device, is irradiated with the plasma blown out from the plasma generating device to modify the surface of the ophthalmic lens to form a final ophthalmic lens product.

31 Claims, 12 Drawing Sheets

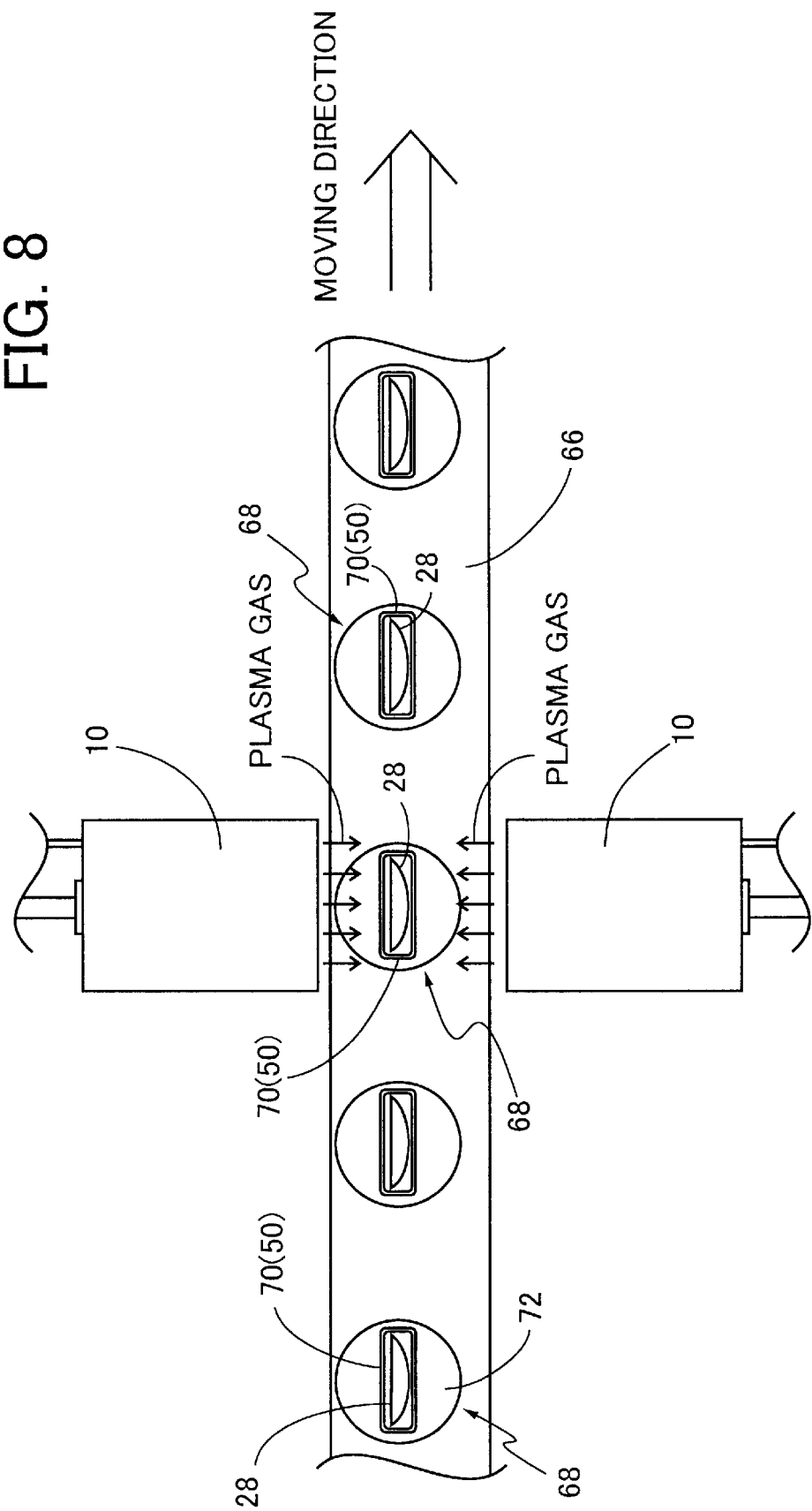

METHOD OF MODIFYING OPHTHALMIC LENS SURFACE BY PLASMA GENERATED AT ATMOSPHERIC PRESSURE

This application is based on Japanese Patent Application Nos. 2000-306155 filed Oct. 5, 2000, and 2001-239599 filed Aug. 7, 2001, the contents of which are incorporated hereinto by reference.

BACKGROUND OF THE INVENTION

1. Field of the Invention

The present invention relates to a method of modifying or treating a surface of an ophthalmic lens. More particularly, the present invention is concerned with a method of modifying the ophthalmic lens surface by irradiating the ophthalmic lens surface with plasma generated at an atmospheric pressure, for thereby improving the properties of the ophthalmic lens surface such as wettability or hydrophilicity.

2. Discussion of Related Art

For assuring a lens user of excellent wear comfort of an ophthalmic lens such as a contact lens while eliminating a feeling of discomfort during wear of the ophthalmic lens, various techniques are proposed to modify a surface of the ophthalmic lens, for thereby improving wettability of the surface of the ophthalmic lens to attain a high degree of compatibility of the lens surface with the tear fluid of the eye, and the cornea surface of the eye.

Japanese Patent No. 2846343 discloses a method of giving wettability to a surface of an oxygen permeable hard contact lens, by subjecting the contact lens to a high-frequency glow discharge treatment at a reduced pressure in an atmosphere which does not include oxygen. JP-A-3-220519 discloses a method of improving wettability of a contact lens, by first subjecting a contact lens material to a discharge treatment at a normal or reduced pressure to generate free radicals on the surface of the contact lens material, and then effecting graft polymerization of N,N-dimethylacrylamide on the surface of the contact lens material on which the free radicals are generated.

The former method described above wherein the high-frequency glow discharge treatment is effected at a reduced pressure in an atmosphere not including oxygen, however, requires steps of replacing the ambient air in a container accommodating the contact lens, with the atmosphere which does not include oxygen, and evacuating the container after the contact lens has been accommodated therein. Accordingly, the disclosed method cannot utilize the ambient air for modifying the contact lens surface, and has a low degree of working efficiency, undesirably pushing up the cost of the surface modification of the contact lens. In the latter method, the contact lens material is initially subjected to the discharge treatment, and subsequently to the graft polymerization, so that the process steps for modifying the surface of the contact lens material are more complicated than those in the former method. Further, the cost of manufacture of the contact lens is inevitably increased.

It is known that the discharge treatment (plasma treatment) described above assures a sterilizing effect as well as improved wettability. JP-A-8-156920 discloses a method of sterilizing a subject formed of a synthetic or a natural high-molecular material by a glow discharge treatment at an atmospheric pressure while the subject is interposed between the electrodes which are opposed to each other. This method attains effective sterilization with respect to bacteria and spores.

Even if the above-described sterilizing method is applied to the ophthalmic lens for simultaneously modifying and sterilizing the ophthalmic lens surface, it requires a cumbersome step of iteratively disposing the subjects (contact lenses) to be treated in a limited space defined by and between the electrodes for effecting the discharge treatment on the subjects, making it difficult to modify, in a short period of time, the surfaces of the contact lenses which are mass-produced. Further, the above-described sterilizing method may cause insufficient modification of the contact lens surfaces since the treatment is effected in the atmosphere between the electrodes. Moreover, the contact lens surfaces may not be uniformly modified due to a variation of the density of the plasma gas to which the contact lenses are exposed.

SUMMARY OF THE INVENTION

The present invention was developed in the light of the background art situations described above. It is therefore an object of the present invention to provide a method of modifying a surface of an ophthalmic lens by contacting the surface of the ophthalmic lens with plasma generated at an atmospheric pressure, wherein the ophthalmic lens surface can be uniformly modified with high degrees of working efficiency and economy without damaging the ophthalmic lens.

The object indicated above may be achieved according to a first aspect of the present invention, which provides a method of modifying a surface of an ophthalmic lens, including the steps of: generating plasma at an atmospheric pressure; and contacting the ophthalmic lens with the plasma for modifying the surface of the ophthalmic lens.

In the present method indicated above wherein the plasma is generated at an atmospheric pressure and the ophthalmic lens is brought into contact with the plasma, the surface of the ophthalmic lens can be modified so as to improve its wettability or hydrophilicity without evacuating the container in which the ophthalmic lens is accommodated, for thereby significantly improving the working efficiency while decreasing a time and a cost required for modifying the ophthalmic lens surface. Further, the present method does not require any equipment (e.g., gas conduit and working gas) for replacing the ambient air in the container with a suitable atmosphere resulting in reduction of an equipment cost.

In one preferred form of the above-indicated first aspect of the present invention, the step of contacting the ophthalmic lens with the plasma comprises a step of blowing the plasma onto the ophthalmic lens through at least one opening of a plasma control member which is spaced apart from the surface of the ophthalmic lens.

In one advantageous mode of the above preferred form of the first aspect of the invention, the plasma control member has a matrix of a multiplicity of openings. Preferably, the plasma control member is a network which has a matrix of a multiplicity of openings each having a size of 0.3~15 mm. The network is preferably a wire framework consisting of a plurality of wires each having a diameter of 0.1~3 mm. Preferably, the plasma control member is a planar member which has a matrix of a multiplicity of perforations formed through a thickness thereof. The planar member preferably has an opening ratio of 15~70%, and is a sheet member which has perforations formed by punching and which has a thickness in a range of 0.1~3 mm.

The object indicated above may be achieved according to a second aspect of the invention, which provides a method of modifying a surface of an ophthalmic lens, including the steps of: generating plasma at an atmospheric pressure between electrodes of a plasma generating device; and blowing the plasma from the plasma generating device by introducing a gas between the electrodes, so as to irradiate the ophthalmic lens located outside the plasma generating device with the plasma blown out from the plasma generating device for modifying the surface of the ophthalmic lens.

In the present method described above, the ophthalmic lens to be treated is disposed outside the electrodes of the plasma generating device, and the plasma generated at an atmospheric pressure between the electrodes is forced to be blown onto the ophthalmic lens by introducing a gas between the electrodes. This arrangement eliminates the conventionally required cumbersome step of iteratively disposing a predetermined number of ophthalmic lenses within a limited space between the electrodes, resulting in a speedy treatment of the ophthalmic lens. Accordingly, the present method assures high efficiency and economy in modifying the ophthalmic lens surface.

The present method wherein the plasma generated between the electrodes is blown onto the ophthalmic lens by the gas introduced between the electrodes is unlikely to suffer from variation in the density of plasma gas blown out from the plasma generating device, so that the ophthalmic lens surface can be uniformly modified.

In one preferred form of the above second aspect of the invention, the method further includes a step of interposing a plasma control member between the ophthalmic lens and the plasma generating device, and wherein the plasma is blown onto the ophthalmic lens through at least one opening of the plasma control member.

In this arrangement wherein the plasma generated at the atmospheric pressure is blown onto the ophthalmic lens through at least one opening of the plasma control member, portions of the plasma contact or collide with the plasma control member in the vicinity of the at least one opening before passing through the opening, whereby the plasma is blown onto the ophthalmic lens in various directions which include the direction in which the plasma is initially blown out from a suitable plasma generating device. Since the plasma which has passed through the at least one opening of the plasma control member is blown onto the ophthalmic lens in the various directions, the plasma is unlikely to concentrate on the peripheral portion (edge portion) of the ophthalmic lens, and arcs tend to generate near the plasma control member instead of the edge portion of the ophthalmic lens. Accordingly, the present method prevents the edge portion of the ophthalmic lens from suffering from a phenomenon similar to an arc discharge, for thereby effectively preventing damaging or cracking of the lens body.

In the present method wherein the plasma is generated at the atmospheric pressure between the electrodes of the plasma generating device and the ophthalmic lens is brought into contact with the plasma, the surface of the ophthalmic lens can be modified so as to improve its wettability or hydrophilicity without evacuating the container in which the ophthalmic lens is accommodated, for thereby significantly improving the working efficiency while decreasing a time and a cost required for modifying the ophthalmic lens surface. Further, the present method does not require any equipment (e.g., gas conduit and working gas) for replacing the ambient air in the container with a suitable atmosphere, resulting in reduction of an equipment cost.

In one advantageous mode of the above preferred form of the second aspect of the invention, the plasma control member has a matrix of a multiplicity of openings. Preferably, the plasma control member is a network which has a matrix of a multiplicity of openings each having a size of 0.3~15 mm. The network is preferably a wire framework consisting of a plurality of wires each having a diameter of 0.1~3 mm. Preferably, the plasma control member is a planar member which has a matrix of a multiplicity of perforations formed through a thickness thereof. The planar member preferably has an opening ratio of 15~70%, and is a sheet member which has perforations formed by punching and which has a thickness in a range of 0.1~3 mm.

In another preferred form of the above-described second aspect of the invention, the step of blowing the plasma is effected on at least one ophthalmic lens while the at least one ophthalmic lens is moved relative to the plasma generating device by a conveyor. According to this arrangement, the at least one ophthalmic lens is continuously moved or transferred by the conveyor to the position at which the surface of the ophthalmic lens is modified by the plasma blown from the plasma generating device, so that the ophthalmic lens is effectively treated by the plasma, resulting in high working efficiency and economy.

In still another preferred form of the above-described second aspect of the invention, the step of blowing the plasma is effected while the ophthalmic lens is held by a flexible lens holder. According to this arrangement, the ophthalmic lens is prevented from being blown off by the plasma or protected from deformation due to a strong flow of the plasma gas blown out from the plasma generating device, effectively protecting the ophthalmic lens from being damaged.

Preferably, the plasma is blown out from the plasma generating device in a direction which is perpendicular to an optical axis of the ophthalmic lens, so that the plasma flows laterally on the ophthalmic lens. In this arrangement, the entire surface of the ophthalmic lens, e.g., a front and a back surface of the contact lens, is irradiated with the plasma, assuring uniform surface modification of the ophthalmic lens.

Preferably, the plasma is blown onto one of opposite surfaces of the ophthalmic lens in a direction parallel to an optical axis of the ophthalmic lens. According to this arrangement, one of opposite surfaces of the ophthalmic lens, e.g., one of the front and back surfaces of the contact lens, can be entirely and uniformly irradiated with the plasma. Preferably, the plasma is blown onto opposite surfaces of the ophthalmic lens in opposite directions which are parallel to the optical axis of the ophthalmic lens. According to this arrangement, the opposite surfaces of the ophthalmic lens, e.g., both of the front and back surfaces of the contact lens, can be entirely and uniformly irradiated with the plasma.

In yet another preferred form of the second aspect of the invention, the gas introduced between the electrodes of the plasma generating device is selected from the group consisting of nitrogen, oxygen, helium, neon, argon, and mixtures thereof. Alternatively, the atmospheric air is preferably introduced between the electrodes.

Preferably, the ophthalmic lens is irradiated with the plasma for a time period in a range between 0.01 second and 180 seconds, and the ophthalmic lens is preferably a contact lens.

In a further preferred form of the second aspect of the invention, the ophthalmic lens is formed in a mold cavity defined by and between two molds of a mold assembly, and the plasma is blown on one of opposite surfaces of the ophthalmic lens while it is held by one of the two molds which have been separated away from each other, so that the one of opposite surfaces of the ophthalmic lens which has been removed from the other of the two molds is irradiated with the plasma. According to this arrangement, a desired one of opposite surfaces of the ophthalmic lens can be modified while the ophthalmic lens is held with high stability by one of the two molds.

Preferably, the plasma is generated by a glow discharge. Further, the surface of the ophthalmic lens is preferably sterilized by irradiation of the plasma. Preferably, the gas is introduced between the electrodes of the plasma generating device after the gas is in contact with hydrogen peroxide water. By using the gas which has been in contact with hydrogen peroxide water, the ophthalmic lens surface can be effectively sterilized.

The present invention is also directed to an ophthalmic lens whose surface is modified according to the methods as described above.

BRIEF DESCRIPTION OF THE DRAWINGS

The above and other objects, features, advantages and technical and industrial significance of the present invention will be better understood by reading the following detailed description of presently preferred embodiments of the invention, when considered in connection with the accompanying drawings, in which:

FIG. 8 is a view showing a system of successively modifying the ophthalmic lens surface by using the device of FIG. 1;

DETAILED DESCRIPTION OF THE INVENTION

Figure 1:
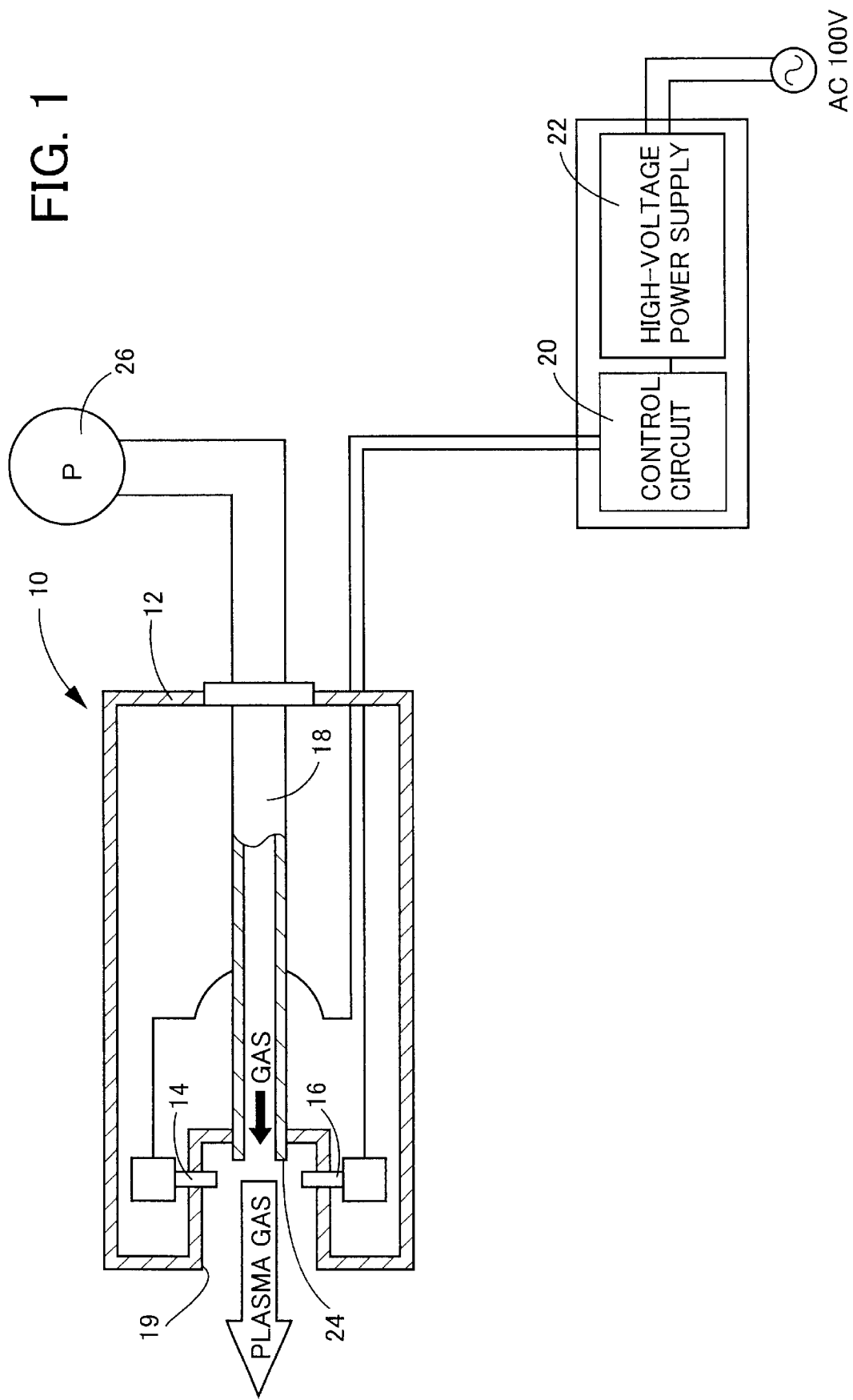
FIG. 1 is an elevational view partly in cross section schematically showing a plasma generating device used in modifying the ophthalmic lens surface according to the present invention.

Referring first to FIG. 1, there is shown a plasma generating device used for modifying a surface of an ophthalmic lens according to the present invention. In FIG. 1, a head 10 of the plasma generating device includes a box-like chamber 12, in which there are accommodated electrodes 14, 16 for generating plasma therebetween, and a gas conduit 18 through which a working gas flows for blowing off the plasma generated between the electrodes 14, 16 outside the chamber 12. By introducing the gas between the two electrodes 14, 16, the generated plasma is blown out from a plasma outlet 19 of the plasma generating device, so that the ophthalmic lens which is located outside the plasma generating device is brought into contact with or irradiated with the plasma blown out from the plasma generating device.

Described more specifically, a suitable voltage is applied between the two electrodes 14, 16 from a high-voltage power supply 22 via a control circuit 20, for thereby inducing a discharge at an atmospheric pressure in the presence of air or a suitable gas between the electrodes 14, 16. The voltage applied between the electrodes 14, 16 is generally in a range between 10 kV and 20 kV, for establishing a stable glow discharge. If the applied voltage is lower than 10 kV, the electric field is unstable. Accordingly, the ophthalmic lens surface which is held in contact with or irradiated with the plasma generated in the unstable electric field cannot be uniformly modified. Further, it undesirably takes a relatively long period of time to modify the ophthalmic lens surface. On the other hand, if the applied voltage is higher than 20 kV, the ophthalmic lens may undergo an arc discharge, and suffer from damage such as cracking.

The frequency of an alternating current supply for applying, between the electrodes 14, 16, the voltage within the range described above is selected from a range between 1 kHz and 200 MHz, preferably between 1 kHz and 100 MHz. The frequency may be 50 Hz or 60 Hz. It requires, however, a large-sized transformer to obtain such a high voltage at the commercially available frequency of 50–60 Hz, causing various problems in view of installation space and safety. By employing such a high frequency held within the range between 1 kHz and 200 MHz, a small-sized transformer can be advantageously used, for thereby reducing the size of the high-voltage power supply 22 and the device as a whole without an increase in the installation space of the device, and assuring a high degree of safety. If the frequency is lower than 1 kHz upon voltage application using the small-sized transformer, it is difficult to apply the voltage not lower than 10 kV necessary for generating the plasma. On the contrary, if the frequency exceeds 200 MHz, the voltage to be applied exceeds the desired upper limit of 20 kV, resulting in an unstable plasma (discharge) condition. In this case, the intended surface modification of the ophthalmic lens will not be attained.

The voltage is applied from the high-voltage power supply 22 between the electrodes 14, 16 via a control device (not shown) which controls the voltage depending upon the kinds, materials, and sizes of individual ophthalmic lenses for optimum surface modification. For instance, the control device preferably controls the voltage such that the voltage is applied with a cycle time of 10–50 milliseconds (ms) and at a duty ratio of 0.1–0.8. The duty ratio is represented as $T_D/T_P$, wherein $T_D$ is a pulse duration and $T_P$ is a pulse repetition period. By pulsing the voltage to be applied to the electrodes 14, 16 and making the application cycle time and the duty ratio variable, the degree of the surface modification of the ophthalmic lens by the plasma can be varied as desired. If the application cycle time is larger than 50 milliseconds and the duty ratio is less than 0.1, it is difficult to maintain a plasma condition suitable for the surface modification. On the other hand, if the application cycle time is smaller than 10 milliseconds and the duty ratio exceeds 0.8, the surface of the ophthalmic lens may be excessively modified. In this case, it requires fine or precise control of the irradiation time of the plasma. It is, however, difficult in general to control the irradiation time of the plasma in steps of 0.1 millisecond.

The plasma generated between the electrodes 14, 16 by application of the voltage therebetween is blown out from the head 10 of the plasma generating device via a plasma outlet 19 by the gas fed from an outlet 24 of the gas conduit 18. More specifically described, a suitable gas is supplied at a predetermined flow rate by a pump 26 located outside the head 10 of the plasma generating device. The gas flows through the gas conduit 18, and is jetted from the gas outlet 24 towards the spacing between the two electrodes 14, 16. The gas jetted from the outlet 24 blows the plasma generated between the electrodes 14, 16 outside the plasma generating device.

Examples of the gas introduced between the two electrodes 14, 16 include nitrogen, oxygen, helium, neon, argon, and mixtures thereof. Since the plasma is generated at the atmospheric pressure, the atmospheric air can be used as the working gas for blowing the generated plasma out from the plasma generating device. The use of the atmospheric air is effective to considerably reduce the cost required for the surface modification of the ophthalmic lens. The rate at which the gas is jetted or discharged from the outlet 24 is not particularly limited, but may be suitably determined as necessary. Preferably, the gas is discharged at a rate of 0.1~200 L/minute, more preferably 0.1~100 L/minute. If the discharge rate is less than 0.1 L/minute, the amount of radiation of the plasma is not enough for sufficient surface modification of the ophthalmic lens. On the other hand, if the discharge rate exceeds the upper limit of 200 L/minute, the amount of radiation of the plasma is excessively large, undesirably causing damage such as cracking on the lens surface.

Figure 2:
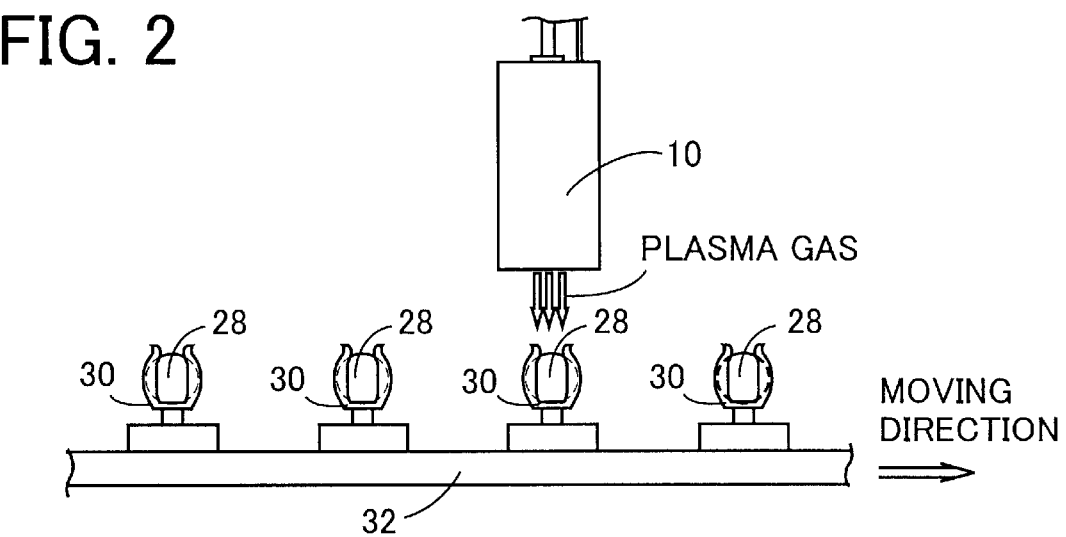
FIG. 2 is a view showing a system of modifying the ophthalmic lens surface according to one embodiment of the invention by using the device of FIG. 1.

The plasma gas blown out from the plasma outlet 19 is blown onto the ophthalmic lens (a contact lens 28 in the present embodiment) located outside the plasma generating device and held by a suitable lens holder, as shown in FIG. 2. The present embodiment wherein the generated plasma is blown out from the space between the electrodes 14, 16 of the plasma generating device, eliminates the conventionally required cumbersome step of iteratively disposing a predetermined number of ophthalmic lenses within the limited space between the electrodes, for thereby reducing the required time for the surface modification and assuring a high degree of working efficiency. Moreover, the plasma blown onto the ophthalmic lens is less likely to suffer from a variation in its density, so that the ophthalmic lens surface can be uniformly modified.

In the present embodiment, the plasma is blown onto the contact lens 28 which is held by a flexible lens holder 30 (FIGS. 3 and 4) similar in construction to those disclosed in JP-U-A-50-20652, JP-U-B-1-43697 and JP-U-A-62-35326. Accordingly, the contact lens 28 is prevented from being blown off upon exposure to the plasma gas or protected from deformation or bending by the lens holder due to an excessive stress of the plasma gas acting on the lens.

Figure 3:
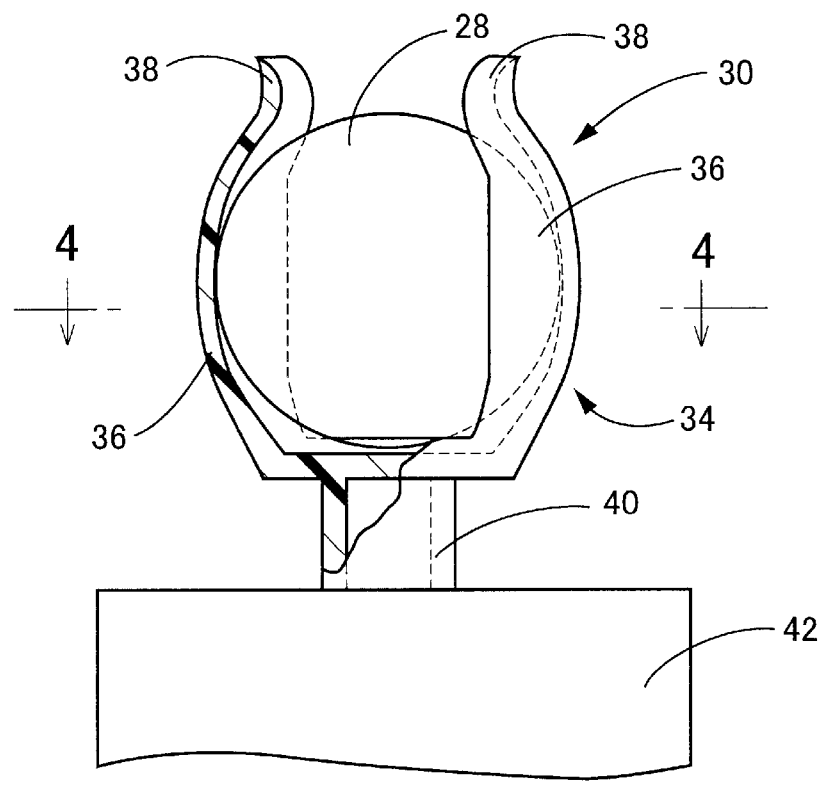
FIG. 3 is a front elevational view partly in cross section showing a flexible lens holder used in the system of FIG. 2.
Figure 4:
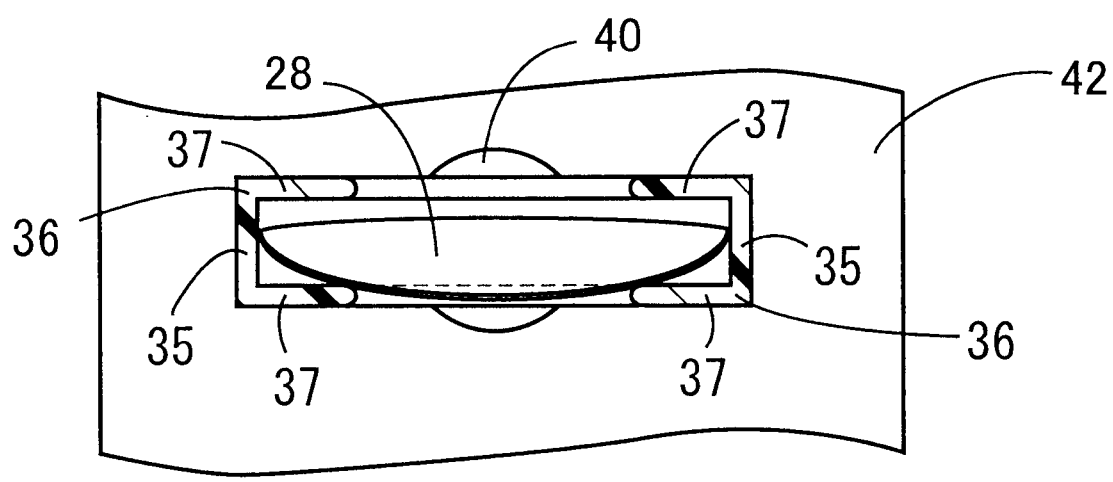
FIG. 4 is a cross sectional view taken along line 4—4 of FIG. 3.

The lens holder 30 shown in FIGS. 3 and 4 includes a holding portion 34 in which the contact lens 28 is accommodated. The holding portion 34 is formed of a resin material having suitable degrees of elasticity and flexibility, for thereby protecting the contact lens 28 from being subjected to the excessive stress of the plasma gas.

Described more specifically, the lens holder 30 consists of the flexible holding portion 34, a support rod 40 formed integrally with the holding portion 34, and a base 42 to which the support rod 40 is fixed. The holding portion 34 consists of a pair of arms 36, 36 which are connected integrally with each other at their proximal ends on the side of the support rod 40. As shown in FIG. 4, each arm 36 consists of an arcuate outer wall 35 and two side walls 37, which cooperate to form a U-shaped configuration in cross section. The arms 36 are opposed to each other with a suitable space therebetween for accommodating the contact lens therein. The distal end of the outer wall 35 of each arm 36 is bent outwards, in other words, in a direction away from the other arm 36 so as to provide a bent portion 38, for easy insertion of the contact lens 28 into the holding portion 34.

A plurality of the lens holders 30 each holding the contact lens 28 are placed on a conveyor 32 which is moved relative to the plasma generating device, such that the lens holders 30 are spaced apart from each other by a suitable distance. Accordingly, the contact lenses 28 are moved relative to the head 10 of the plasma generating device. In this arrangement, the contact lenses 28 are successively and properly placed at a position at which the surface of each lens is modified by the plasma blown from the plasma generating device, permitting successive surface modification treatments of a plurality of contact lenses 28. Therefore, the present arrangement assures high degrees of working efficiency and economy for modifying the surface of the contact lens 28. Any known conveyors such as a belt conveyor, a chain conveyor, an index table and a turntable are used. The conveyor 32 is moved relative to the head 10 of the plasma generating device at a rate of about 0.05~1000 mm/sec, preferably about 1~100 mm/sec. If the conveyor 32 is moved relative to the plasma generating device at a rate lower than 0.05 mm/sec, the ophthalmic lens tends to suffer from cracking. On the other hand, if the relative speed of the conveyor 32 with respect to the plasma generating device exceeds 1000 mm/sec, the ophthalmic lens surface is not modified by the plasma blown from the plasma generating device.

In the present arrangement shown in FIG. 2, each contact lens 28 is held by the lens holder 32 such that its optical or geometrical center axis extends in the horizontal direction, and is perpendicular to the direction in which the contact lens 28 is moved by the Conveyor 32. For effecting the surface modification of the contact lens 28, the plasma generating device is disposed such that the plasma outlet 19 is located above the contact lens 28 held by the lens holder 30 shown in FIG. 2, so that the plasma is blown out from the plasma generating device in a direction parallel to the surface of the contact lens 28, whereby the plasma flows laterally on the contact lens 28. According to this arrangement, both of the front and back surfaces of the contact lens 28 are entirely exposed to the plasma gas, resulting in uniform surface modification.

The surface modification method according to the present embodiment is applicable to any known ophthalmic lenses including contact lenses (28) such as a silicon-containing hydrogel soft contact lens, a silicon-containing non-water-absorptive soft contact lens, a silicon-containing gas permeable hard contact lens, and an intraocular lens formed of a polymer whose major component is ethylmethacrylate.

For irradiating the contact lens 28 with the plasma gas blown out from the plasma generating device, it is desirable that the shortest distance (work distance) between the edges of the electrodes 14, 16 and the contact lens 28 be in a range of 3~200 mm, more preferably 3~100 mm. If the work distance is less than 3 mm, the desired surface modification by irradiation of the plasma is not attained. On the other hand, if the work distance exceeds 200, mm, the surface area of the contact lens 28 modified by plasma decreases with an increase of the work distance. In this case, the surface of the contact lens 28 cannot be modified by the plasma as desired.

The ophthalmic lens is irradiated with the plasma gas for a time period in a range between 0.01 second and 180 seconds, for attaining a sufficiently high degree of surface modification so as to give the ophthalmic lens a sufficiently high degree of wettability. If the irradiation time of the plasma is less than 0.01 second, the surface of the ophthalmic lens cannot be modified by the plasma, and on the other hand, the ophthalmic lens may suffer form damage such as cracking if the irradiation time of the plasma exceeds 180 seconds. The surface modification effect by irradiation of the plasma is considerably high especially when the ophthalmic lens is irradiated with the plasma for more than 1 second. When the irradiation time of the plasma is not more than 10 seconds, a plurality of ophthalmic lenses can be successively subjected to the surface modification treatment, for thereby permitting speedy surface modification of the contact lenses 28. In view of this, the irradiation time of the plasma is particularly preferably held in a range between 1 second and 10 seconds. When the irradiation time is longer than 10 seconds, an increase in an oxygen ratio on the surface of the ophthalmic lens is kept constant, and a sufficient degree of the surface modification by the plasma is attained. Accordingly, the irradiation time of the plasma up to 10 seconds is enough according to the present invention.

As is apparent from the above description, the ophthalmic lens in the form of the contact lens 28 is subjected to the plasma (glow discharge) treatment at the atmospheric pressure, so that the present embodiment assures an improved surface modification effect and renders the contact lens surface hydrophilic to enhance the wettability of the surface, as effectively as, or more effectively than the conventional arrangement wherein the surface modification of the contact lens is effected by the low-pressure glow discharge, or the corona discharge at the atmospheric pressure. Moreover, the contact lens can be sterilized at the same time when the surface is modified by the plasma.

The present embodiment wherein the surface modification is effected by the glow discharge at the atmospheric pressure eliminates the conventionally required step of evacuating the container in which the ophthalmic lens is accommodated, for thereby significantly improving the working efficiency while decreasing the time and cost of modifying the ophthalmic lens surface. Further, the present arrangement does not require any equipment (e.g., gas conduit and working gas) for replacing the ambient air in the container with a suitable atmosphere, resulting in reduction of the equipment cost.

In the present embodiment, the plasma (glow discharge) is generated between the electrodes while the ophthalmic lens whose surface is to be modified is located outside the space between the electrodes (cathode and anode). The thus generated plasma is forcibly blown onto the ophthalmic lens located outside the electrodes, by introducing the gas between the electrodes, for thereby permitting uniform surface modification in a relatively short period of time. In the present embodiment, the plasma generating device is disposed independently of the carrier system in the form of the belt conveyor on which a plurality of ophthalmic lenses are placed such that the lenses are equally spaced apart from each other. Accordingly, the present embodiment permits a simplified arrangement of the system for the surface modification of the ophthalmic lens in a reduced installation space. Since the carrier system does not move between the electrodes of the plasma generating device, the carrier system does not suffer from any damage due to the plasma.

Figure 5:
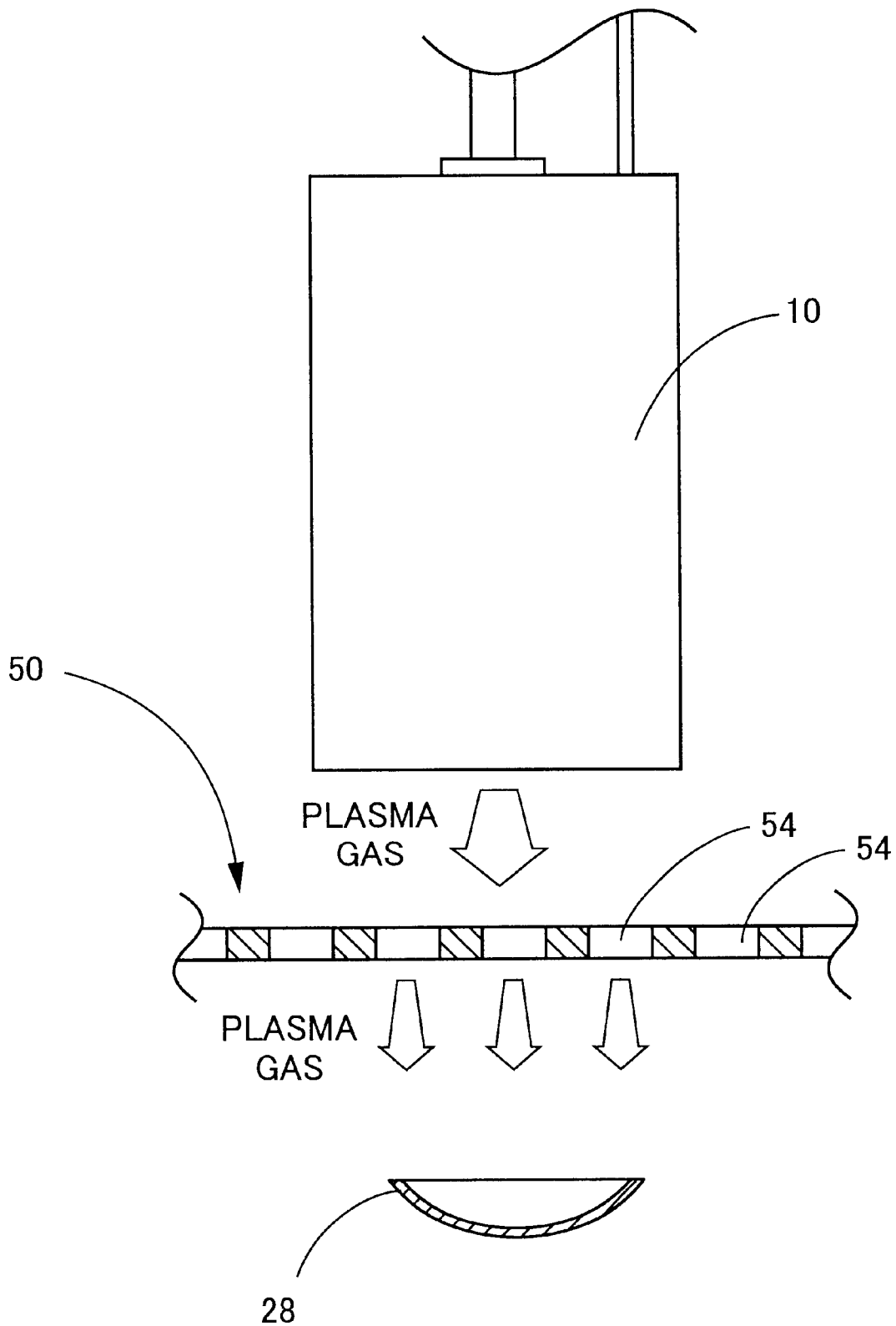
FIG. 5 is an elevational view partly in cross section showing an arrangement for modifying the ophthalmic lens surface according to another embodiment of the invention.

In irradiating the contact lens 28 with the plasma, a suitable plasma control member may be interposed between the contact lens 28 and the head 10 of the plasma generating device as shown in FIG. 5. In this second embodiment shown in FIG. 5, the plasma control member in the form of a planar member 50 having a multiplicity of perforations 54 is interposed between the contact lens 28 and the head 10 of the plasma generating device, such that the planar member 50 is spaced apart from one of opposite surfaces (back surface in FIG. 5) of the contact lens 28. The perforations 54 are formed through the thickness of the planar member 50, and have a prescribed diameter. The contact lens 28 is exposed to portions of the plasma blown out from the head 10 of the plasma generating device, which portions have passed through the perforations 54 of the planar member 50, so that the surface of the contact lens 28 is modified.

In this second embodiment, the plasma generating device (FIG. 1) as used in the illustrated first embodiment is used to modify the surface of the contact lens 28. In the present embodiment wherein the planar member 50 as the plasma control member is interposed between the head 10 of the plasma generating device and the contact lens 28, portions of the plasma blown out from the head 10 of the plasma generating device contact or collide with the planar member 50 in the vicinity of the perforations 54 before passing through the perforations 54, for thereby allowing the plasma to flow in various directions which include the direction in which the plasma is initially blown out from the head 10 of the plasma generating device. Therefore, the plasma is blown onto the surface of the contact lens 28 in the various directions.

In the present embodiment wherein the planar member 50 is interposed between the contact lens 28 and the head 10 of the plasma control member as described above, the contact lens 28 does not suffer from, at its edge portion, the phenomenon which is similar to the arc discharge and which arises from concentration of the plasma on the edge portion of the contact lens. Such phenomenon takes place only in the vicinity of the perforations 54 of the planar member 50. Accordingly, the contact lens 28 is effectively prevented from being damaged.

In the present embodiment, the contact lens 28 is irradiated with the plasma while it is held by a suitable lens holder, so that the contact lens 28 is prevented from being blown off upon exposure to the plasma gas or protected from deformation or bending by the holder due to an excessive stress of the plasma gas acting on the lens. The lens holder is preferably formed of a resin material which exhibits flexibility. For instance, various known lens holders including the lens holder (FIGS. 3 and 4) used in the illustrated first embodiment are preferably used.

The surface modification of the contact lens 28 is effected under the same conditions as in the above-described first embodiment. Namely, the voltage to be applied between the electrodes and the frequency of the alternate power supply are determined to be selected from the respective preferred ranges described above. The cycle time and the duty ratio for applying the voltage between the electrodes of the plasma generating device are also selected from the respective preferred ranges described above. The gas to be introduced between the electrodes is selected from those described above with respect to the above-described first embodiment, and the flow rate of the selected gas is determined to be within the preferred range described above. Further, the work distance between the contact lens to be modified and the edges of the electrodes, and the irradiation time of the plasma are selected from the respective preferred ranges described above.

Figure 6:
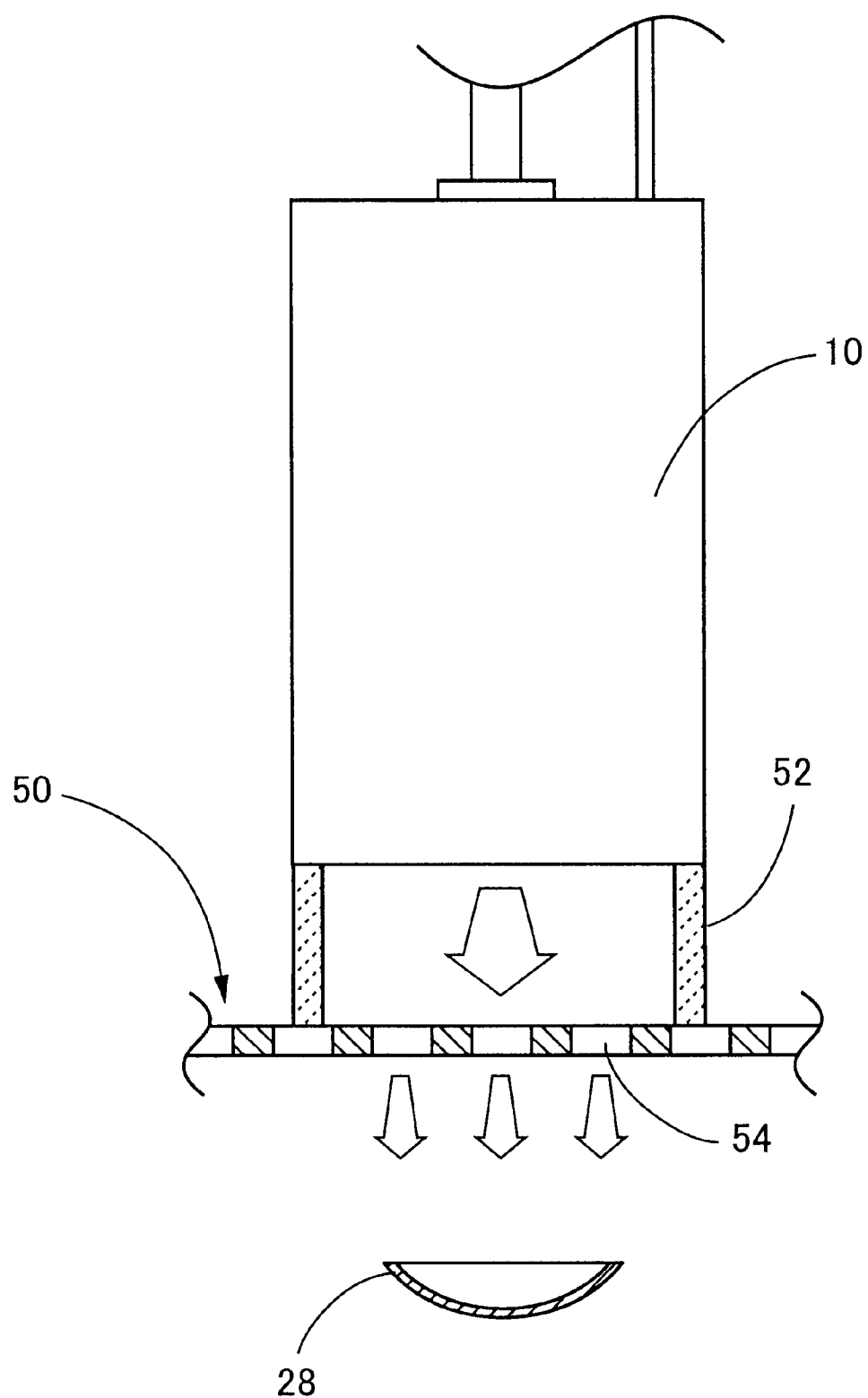
FIG. 6 is an elevational view partly in cross section showing the plasma control member fixed to the plasma generating device via the glass tube.

The plasma control member in the form of the planar member 50 with perforations 54 is fixedly positioned between the head 10 of the plasma generating device and the contact lens 28 by any means known in the art. For instance, a glass tube 52 having a diameter large enough to surround the plasma outlet 24 and a suitable length as shown in FIG. 6 is disposed between the head 10 and the planar member 50, such that one of opposite annular end faces of the glass tube 52 is fixed to the head 10 and such that the other annular end face is fixed to the planar member 50.

When the planar member 50 is fixed to the head 10 of the plasma generating device by the glass tube 52 as described above, the plasma blown out from the plasma outlet 24 of the head 10 of the plasma generating device effectively passes through the perforations 54 of the planar member 50, so that the plasma can be advantageously blown onto the contact lens 28. Moreover, the work distance can be easily determined, in other words, the contact lens to be modified can be easily positioned relative to the head 10 of the plasma generating device. In place of the glass tube 52 described above, other tube members formed of a material which exhibits high degrees of heat-resistance and durability can be used. Such materials for the tube member include a metal such as iron, aluminum, or copper, a fluororesin such as polytetrafluoroethylene, and an engineering plastic such as polyimide or polycarbonate.

Figure 7A:
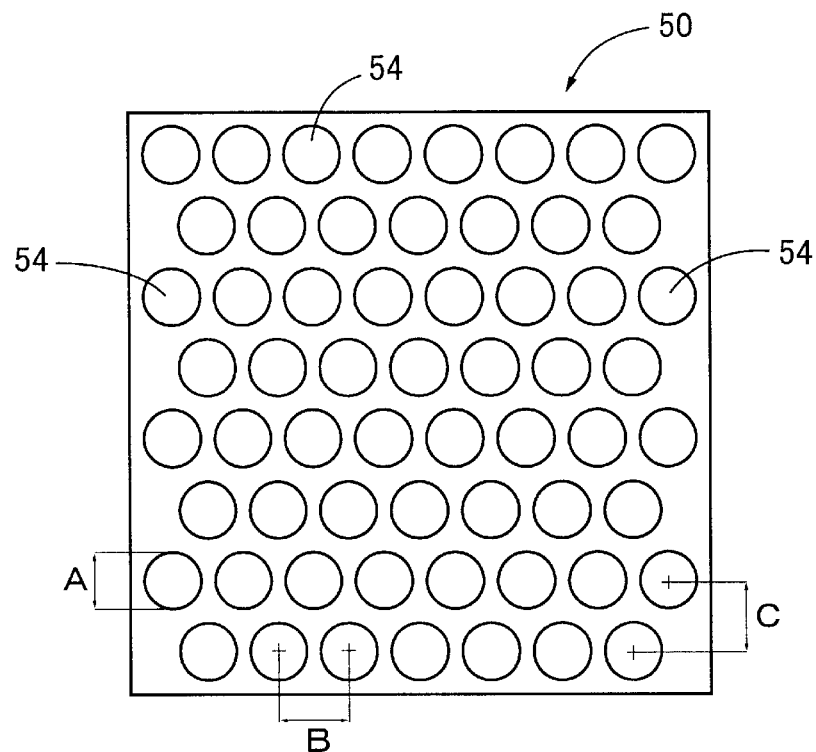
FIG. 7A is a plan view of a planar member as the plasma control member.

The planar member 50 used as the plasma control member in modifying the surface of the ophthalmic lens is shown in FIG. 7A. The planar member 50 has the multiplicity of perforations 54 each of which has a suitable diameter "A". The matrix of the multiplicity of perforations 54 are formed such that the perforations 54 are spaced apart from each other at a pitch "B" in the horizontal direction as seen in FIG. 7A, and at a pitch "C" in the vertical direction as seen in FIG. 7A.

Any known planar members with the perforations which exhibit high degrees of heat-resistance and durability can be used in the present embodiment. For instance, the planar members formed of a meal such as iron, aluminum, or copper, a fluororesin such as polytetrafluoroethylene, and an engineering plastic such as polyimide or polycarbonate are suitably used. If the thickness of the planar member 50 is less than 0.1 mm, the strength of the planar member is insufficient for retaining its shape. The thickness of the planar member exceeding 3 mm makes it difficult to attain uniform surface modification of the ophthalmic lens. In view of this, the thickness of the planar member 50 is generally in a range of 0.1~3 mm, preferably 0.5~1 mm. The shape of each perforation 54 is not limited to the circular shape shown in FIG. 7A, but may be a square, rectangular or any other shape. The size (area) of the perforation 54 is preferably in a range of 0.5~200 mm$^2$, and more preferably in a range of 0.5~150 mm$^2$. If the size of the perforation 54 is smaller than 0.5 mm$^2$, the surface modification effect of the ophthalmic lens by the plasma may be insufficient. On the other hand, when the size of the perforation 54 is larger than 200 mm$^2$, the ophthalmic lens surface cannot be uniformly modified even if the planar member 50 is used. The planar member 50 has an opening ratio, i.e., a ratio of the perforations 54 per unit area, generally in a range of 15~70%, preferably 20~50%. If the opening ratio is smaller than 15%, the surface modification effect by the plasma is insufficient. On the other hand, if the opening ratio is larger than 70%, the ophthalmic lens cannot be uniformly modified even if the planar member 50 is used.

The above-described diameter (A) and pitches (B, C) of the perforations 54 are suitably determined so as to satisfy the requirements described above. In general, it is preferable that all perforations 54 have the same diameter, and that the pitches B and C are made equal to each other.

Figure 7B:
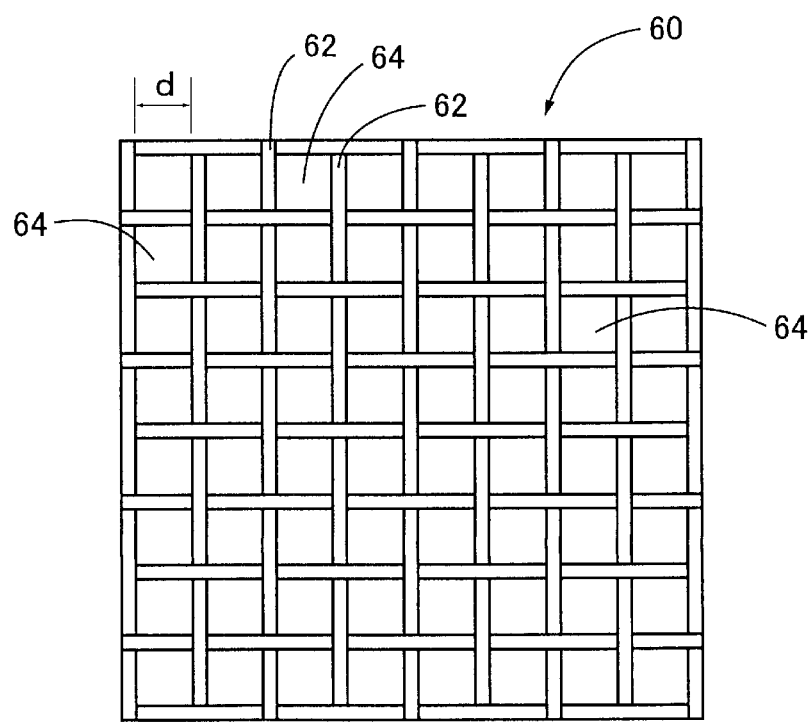
FIG. 7B is a plan view of a network as the plasma control member.
Figure 9:
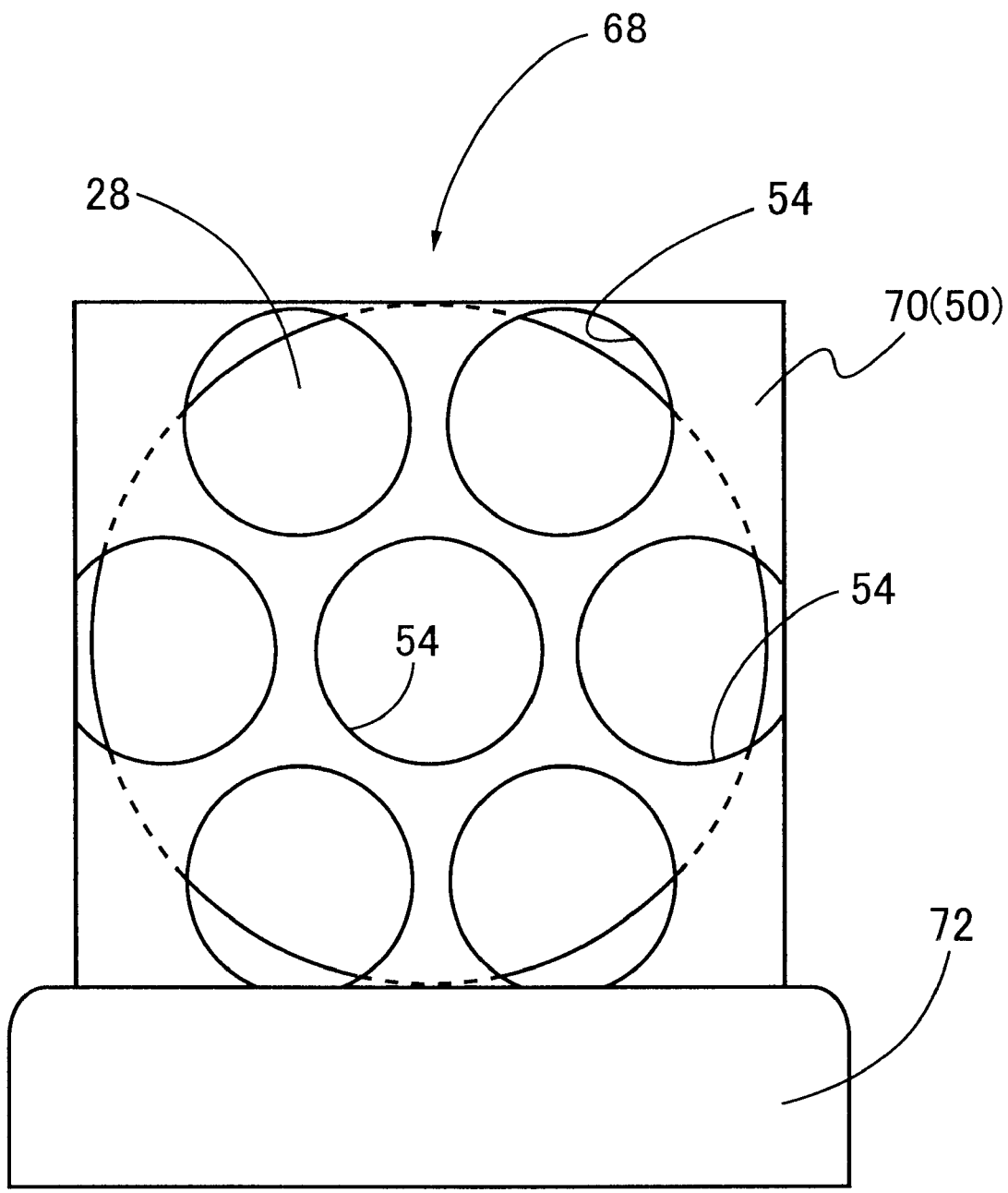
FIG. 9 is a front elevational view showing a lens holder used in the system of FIG. 8.
Figure 10:
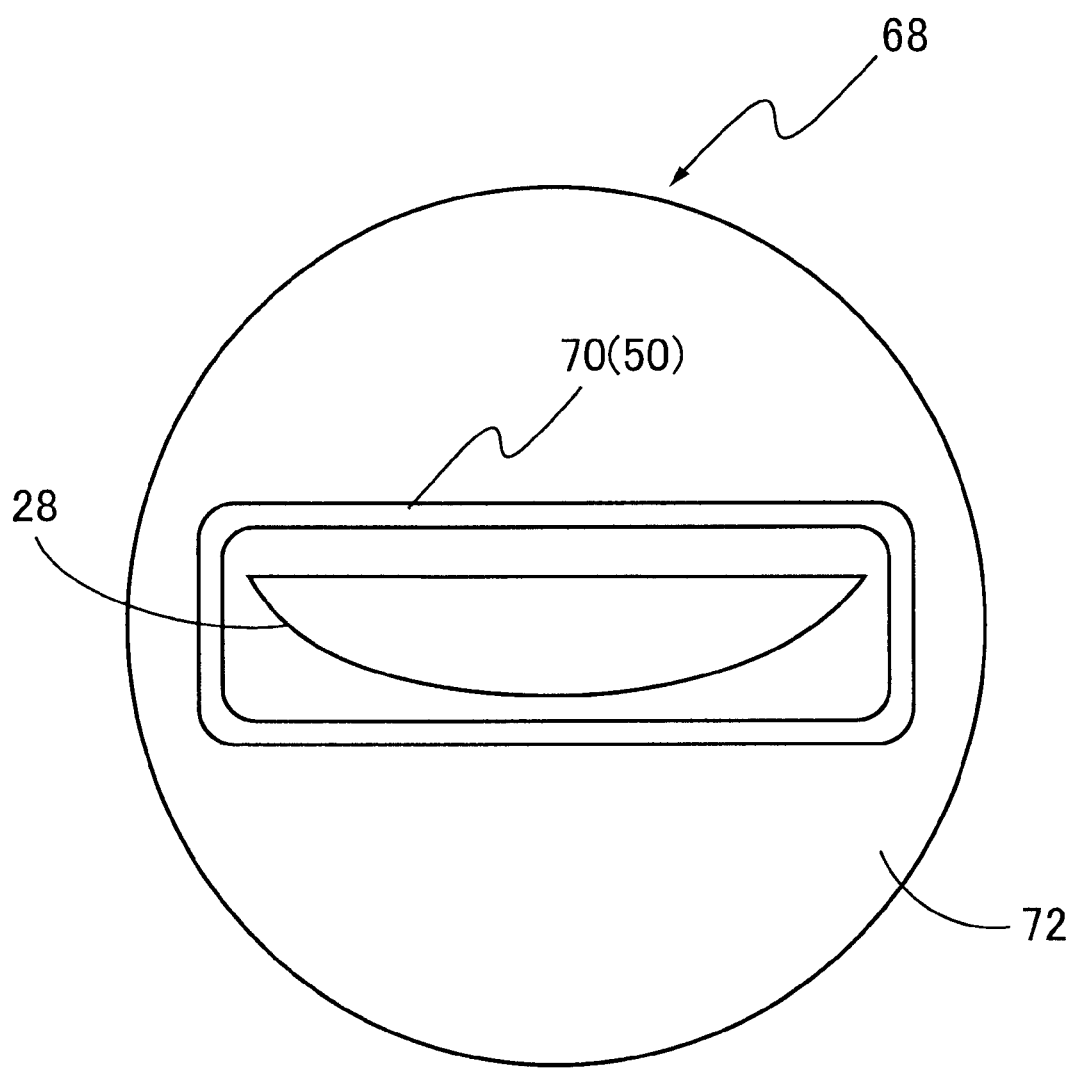
FIG. 10 is a top plan view of the lens holder of FIG. 9.

In place of the planar member 50, a network in the form of a wire framework 60 as shown in FIG. 7B may be used as the plasma control member. The wire framework 60 is a wirework consisting of a plurality of wires 62 having a suitable diameter. The wires 62 are braided, woven or knitted such that the wires 62 cooperate with each other to form a multiplicity of openings 64 each having a constant size "d" shown in FIG. 7B. The plasma is blown onto the ophthalmic lens through the openings 64 of the wire framework 60. Like the planar member 50 having the perforations 54 described above, the wire framework 60 having the openings 64 permits uniform surface modification of the ophthalmic lens while effectively preventing the ophthalmic lens from being damaged at its edge portion.

Any known wire framework consisting of wires formed of a material which exhibits high degrees of heat-resistance and durability can be used in the present embodiment. Examples of such a material include a metal such as iron, aluminum, or copper, a fluororesin such as polytetrafluoroethylene, and an engineering plastic such as polyimide or polycarbonate. Although the size "d" of each opening 64 of the wire framework 60 is suitably determined depending upon the desired degree of the surface modification by the plasma, the size of the opening 64 is preferably in a range of 0.3~15 mm, and more preferably 5~15 mm. If the size of the opening 64 is smaller than 0.3 mm, the surface modification effect by the plasma is insufficient. If the size of the opening 64 is larger than 15 mm, on the other hand, the surface of the ophthalmic lens cannot be uniformly modified even if the wire framework 60 is used. Further, the wires 62 of the wire framework 60 preferably have a diameter of 0.1~3 mm, and more preferably 1~2 mm. When the diameter of the wires 62 is smaller than 0.1 mm, the strength of the wire framework 60 as a whole is lowered, making its handling difficult. When the diameter of the wires 62 is larger than 3 mm, on the other hand, the surface of the ophthalmic lens cannot be uniformly modified even if the wire framework 60 is used.

Referring next to FIG. 8, there is shown a system of modifying the surface of the ophthalmic lens according to the present embodiment. In this system, the two heads 10, 10 of the respective two plasma generating devices are disposed such that the plasma outlets 24 (not shown) of the two plasma generating devices are opposed to each other with a suitable spacing therebetween. Between the two heads 10, 10, there is interposed a conveyor 66 for conveying a plurality of contact lenses 28. Any known conveyors such as a belt conveyor, a chain conveyor, an index table and a turntable are used. On the conveyor 66, a plurality of lens holders 68 for holding the contact lenses 28 are fixed such that the lens holders 68 are equally spaced apart from each other.

More specifically described, each lens holder 68 consists of a base portion 72 and a lens accommodating portion 70 formed on the base portion 72. The lens accommodating portion 70 is formed of the planar member 50 and has a rectangular box-like shape. Within the lens accommodating portion 70, the contact lens 28 is accommodated so that the surface (front and back surfaces) of the contact lens 28 is surrounded by the planar member 50.

A plurality of the lens holders 68 formed as described above are equally spaced apart from each other on the conveyor 66 such that the optical axis of the contact lens 28 held by each lens holder 68 is parallel to the direction in which the plasma is blown from the head 10 of each plasma generating device. The conveyor 66 is moved relative to the heads 10 of the two plasma generating devices.

The plasma gas blown out from the two heads 10, 10 of the respective two plasma generating devices is blown onto the front and back surfaces of the contact lens 28 through the perforations 54 of the planar member 50 which constitutes the lens accommodating portion 70 of the lens holder 68. Accordingly, the opposite surfaces of the contact lens 28 can be uniformly modified while the contact lens 28 is prevented from being damaged.

According to this arrangement, the contact lens 28 held by each lens holder 68 which is placed on the conveyor 66 is moved relative to the heads 10 of the two plasma generating devices, so that the contact lenses 28 are successively and properly placed at a position at which the surface of each lens is modified by the plasma blown from the plasma generating devices, permitting successive surface modification treatments of a plurality of contact lenses 28. Therefore, the present arrangement assures high degrees of working efficiency and economy in modifying the surface of the contact lens 28.

Figure 11:
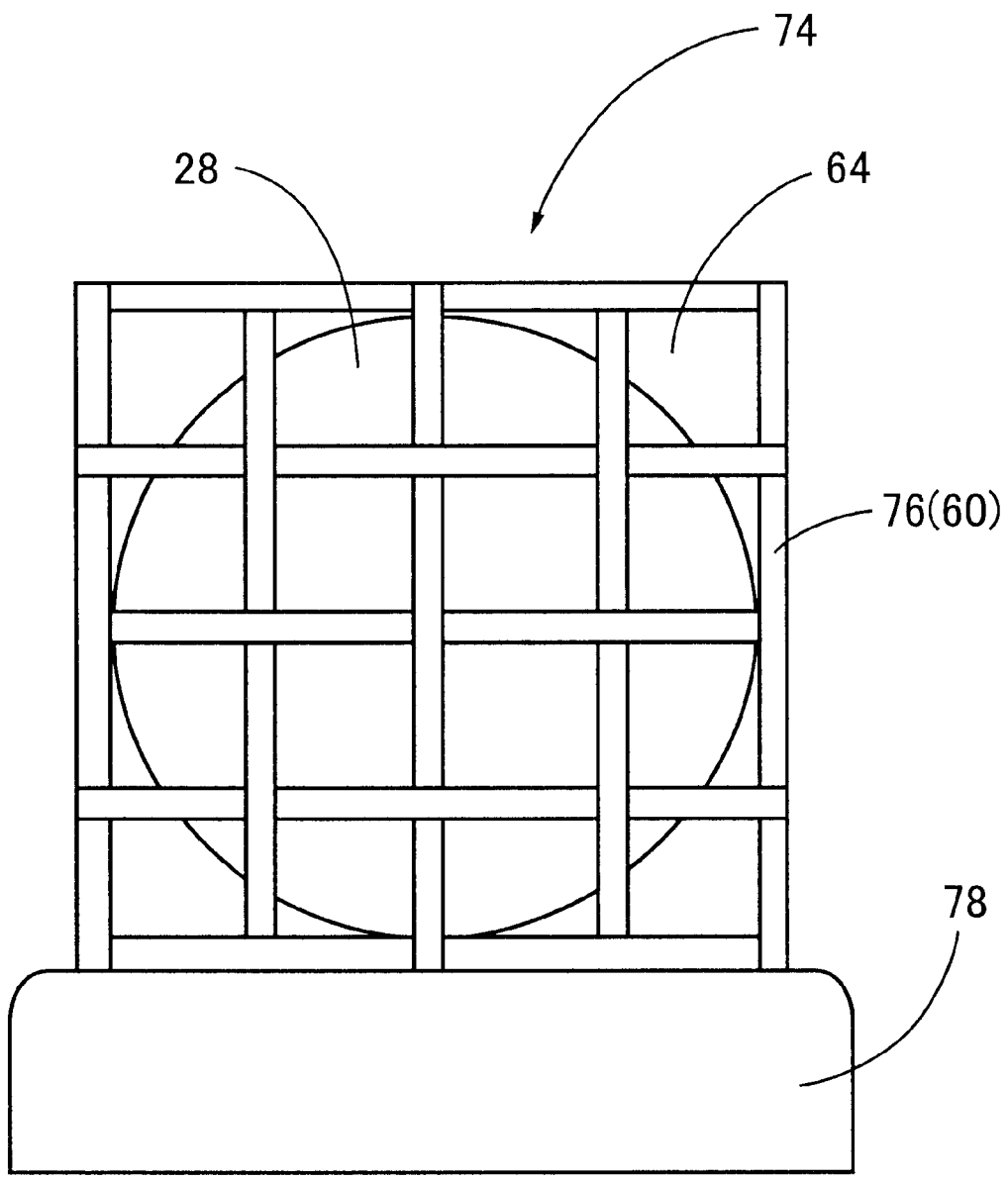
FIG. 11 is a view corresponding to FIG. 9, showing another example of the lens holder.

In place of the lens holder 68 formed of the planar member 50 described above, a lens holder 74 as shown in FIG. 11 may be used. The lens holder 74 of FIG. 11 consists of a base portion 78 and a lens accommodating portion 76 formed on the base portion 78. The lens accommodating portion 76 is formed of the wire framework 60 and has a rectangular box-like shape. Within the lens accommodating portion 76, the contact lens 28 is accommodated so that the surface (front and back surfaces) of the contact lens 28 is surrounded by the wire framework 60. Like the lens holder 68 formed of the planar member 50, the lens holder 74 formed of the wire framework 60 permits effective and uniform surface modification of the contact lens 28 while preventing the contact lens 28 form being damaged.

In the present embodiment, the ophthalmic lens is irradiated with the plasma which has passed through the at least one opening of the plasma control member, that is, at least one of the openings of the wire framework or at least one of the perforations of the planar member. Accordingly, the surface of the ophthalmic lens is effectively modified while preventing the ophthalmic lens from being damaged. The plasma control member is not limited to the wire framework and planar member described above, but may be any other members provided that the members have at least one opening formed through the thickness thereof and that the members assure the effect of the present invention.

The surface modification method according to the present embodiment is applicable to any known ophthalmic lenses including contact lenses (28) such as a silicon-containing hydrogel soft contact lens, a silicon-containing non-water-absorptive soft contact lens, a silicon-containing gas permeable hard contact lens, and an intraocular lens formed of a polymer whose major component is ethylmethacrylate.

In the present embodiment wherein the plasma generated at the atmospheric pressure is blown onto the contact lens (28) as the ophthalmic lens through the at least one opening of the plasma control member, i.e., at least one opening of the wire framework or at least one perforation of the planar member, the surface of the contact lens is uniformly held in contact with the plasma, permitting uniform surface modification of the contact lens while preventing the contact lens from being damaged.

As is apparent from the above description, the ophthalmic lens in the form of the contact lens 28 is subjected to the plasma (glow discharge) treatment at the atmospheric pressure, so that the present embodiment assures an improved surface modification effect and renders the contact lens surface hydrophilic to enhance the wettability of the lens surface, as effectively as, or more effectively than the conventional arrangement wherein the surface modification of the contact lens is effected by the low-pressure glow discharge, or the corona discharge at the atmospheric pressure. Moreover, the contact lens can be sterilized at the same time when the surface is modified by the plasma.

The present embodiment wherein the surface modification is effected by the glow discharge at the atmospheric pressure eliminates the conventionally required step of evacuating the container in which the ophthalmic lens is accommodated, for thereby significantly improving the working efficiency while decreasing the time and cost of modifying the ophthalmic lens surface. Further, the present arrangement does not require any equipment (e.g., gas conduit and working gas) for replacing the ambient air in the container with a suitable gas resulting in reduction of the equipment cost.

While the presently preferred embodiments of this invention have been described in detail by reference to the accompanying drawings, it is to be understood that the invention may be otherwise embodied.

In the illustrated first and second embodiments, the entire surface (front and back surfaces) of the ophthalmic lens in the form of the contact lens 28 is irradiated with the plasma. One of the opposite surfaces of the ophthalmic lens may be modified, as needed. When the ophthalmic lens is formed in a mold cavity defined by and between two molds of a mold assembly, as disclosed in JP-A-10-315252, JP-A-6-208090, JP-A-5-337957, JP-A-55-151618, and JP-U-A-4-89309, for instance, the plasma is blown onto the desired one of opposites surfaces of the ophthalmic lens while the lens is held by one of the two molds which have been separated away from each other, so that the above-indicated one of the opposite surfaces of the ophthalmic lens which has been removed from the other of the two molds is irradiated with the plasma.

In the illustrated first embodiment, a suitable masking member having a desired size and shape may be interposed between the plasma generating device and the ophthalmic lens to be modified. In this case, the ophthalmic lens is irradiated with the plasma, so that the ophthalmic lens surface is partially modified such that only the portion of the ophthalmic lens surface not corresponding to the masking member is modified by the plasma. According to this arrangement, the desired portion of the ophthalmic lens surface can be modified. In this arrangement, it is preferable to arrange such that the masking member is replaceable, so that a desired one of the masking members of different shapes can be used.

In the illustrated first embodiment, the ophthalmic lens (contact lens 28) held by the lens holder 30 is disposed on the conveyor 32 such that the optical or geometrical center axis of the ophthalmic lens is parallel to the horizontal direction, and is perpendicular to the direction in which the conveyor 32 is moved. The ophthalmic lens held by the lens holder 30 may be disposed on the conveyor 32 such that the center axis of the ophthalmic lens is parallel to the vertical direction. In this case, the plasma is blown onto the ophthalmic lens in the horizontal direction, so that the plasma flows laterally on the ophthalmic lens.

The flexible lens holder 30 which holds the ophthalmic lens (contact lens 28) may be designed such that the support rod 40 is rotatable with respect to the base 42 which is fixed to the conveyor 32. This arrangement permits further uniform surface modification of the ophthalmic lens.

The structure of the lens holder is not limited to those of the lens holder 30 in the illustrated first embodiment, and the lens holders 68, 74 in the illustrated second embodiment. The lens holder may be suitably formed depending upon the kind and material of the ophthalmic lens to be modified. The lens holder is not essential unless the ophthalmic lens is blown off by the plasma gas.

In the illustrated first embodiment, the ophthalmic lens (contact lens 28) is irradiated with the plasma blown out from the single head 10 of the single plasma generating device. The ophthalmic lens may be irradiated with the plasma blown out from a plurality of heads of a plurality of plasma generating devices.

In the illustrated first and second embodiments, the ophthalmic lens (contact lens 28) is moved relative to the plasma generating device (10). The plasma generating device (10) may be moved relative to the ophthalmic lens. Further, both of the plasma generating device and the ophthalmic lens may be moved relative to each other.

In the illustrated first and second embodiments, the gas to be introduced between the two electrodes of the plasma generating device is selected from the group consisting of atmospheric air, nitrogen, oxygen, helium, neon, argon, and mixtures thereof. The selected gas may be introduced between the electrodes after the gas is in contact with hydrogen peroxide water, so that the contact lens can be sterilized with high efficiency.

In the illustrated first and second embodiments, any known surface treatments such as a UV irradiation treatment and an ozone surface modification treatment may be effected concurrently with the present surface modification treatment by the plasma.

The lens holding means in the form of the lens holders and the mold of the mold assembly may be provided with a suitable data storage medium in the form of an ID chip or a bar code as disclosed in JP-U-A-6-82923, for instance. The data storage medium stores data of the ophthalmic lens (e.g., specifications of the ophthalmic lens). Based on the data stored in the data storage medium, the plasma irradiation conditions such as the irradiation time, amount, and intensity of the plasma are controlled, for thereby controlling the surface modification treatment depending upon the kinds and specifications of the ophthalmic lens.

In the illustrated second embodiment, the contact lens 28 is held by the lens holders 68, 74 formed of the planar member 50 and the wire framework 60, respectively. In place of these lens holders, various known lens holders including the lens holder 30 (FIGS. 3 and 4) used in the first embodiment may be used for holding the contact lens 28. In this case, the lens holder is surrounded by the planar member 50 or the wire framework 60, so that the contact lens 28 held by the lens holder is irradiated with the plasma blown through at least one perforation of the planar member 50 or at least one opening of the wire framework 60.

In the surface modification system (FIG. 8) of the second embodiment, the plasma is blown out from the two heads 10, 10 of the different two plasma generating devices which are opposed to each other so as to sandwich one contact lens 28 therebetween. According to this arrangement, the opposite surfaces of one contact lens 28 are concurrently exposed to the plasma. The two plasma generating devices may not be located in opposed relation to each other. For instance, one of the two plasma generating devices in FIG. 5 may be located on the upstream or downstream side with respect to the other device, whereby one and the other of the front and back surfaces of two different contact lenses are irradiated, at the same time, with the plasma blown from the respective two plasma generating devices.

EXAMPLES

There will be described some examples of the present invention to further clarify the present invention. It is, however, to be understood that the present invention is not limited to the details of the following examples and the presently preferred embodiments described above, but may be embodied with various changes, modifications and improvements, which may occur to those skilled in the art, without departing from the spirit of the present invention.

Example 1
Surface Modification Effect

As the ophthalmic lens, twelve pieces of silicon-containing gas permeable hard (RGP) contact lenses, and six pieces of silicon-containing hydrogel soft contact lenses were prepared. By using a plasma irradiator "ST-7000" available from KABUSHIKI KAISHA KEYENCE, Japan, as the plasma generating device, the surface of each contact lens was modified under the following conditions:

| | |
|---|---|
| Work distance: | 6 mm |
| Applied voltage: | 10 kV |
| Frequency: | 20~25 kHz |
| Irradiation | |
| Cycle time: | 32 ms |
| Frequency: | 31.25 Hz |
| Duty ratio: | 25% |
| Gas: | atmospheric air |

The surface modification treatment was effected for various time periods with or without the contact lenses being held by a flexible lens holder, as indicated in the following TABLE 1 and TABLE 2. Thus, there were obtained Samples Nos. 1~18 according to the present invention.

For comparison, a silicon-containing RGP contact lens and a silicon-containing hydrogel soft contact lens were prepared as Comparative Samples Nos. 1 and 2, respectively, without being subjected to the plasma treatment.

The thus prepared 20 pieces of contact lens samples were evaluated in terms of wettability, presence of cracking, and oxygen ratio in the following manners.

Evaluation of the Wettability

By using a Goniometer-Type contact angle measuring device ("G-1" available from ELUMA KOGAKU KABUSHIKI KAISHA, Japan), the contact angles were measured by a droplet method for the silicon-containing RGP contact lenses (Samples Nos. 1~12 according to the present invention, and the Comparative Sample No. 1), and by an air bubble method for the silicon-containing hydrogel soft contact lenses (Samples Nos. 13~18 according to the present invention, and the Comparative Sample No. 2). The results are indicated in TABLE 1 and TABLE 2, respectively.

Examination for the Presence of Cracking

The contact lenses according to the Samples Nos. 1~18 of the present invention and the contact lenses according to the Comparative Samples Nos. 1 and 2 were examined for the presence of cracking under a stereomicroscope at 20× (available from KABUSHIKI KAISHA NEITZ, Japan). The results are indicated in the following TABLE 1 and TABLE 2.

Measurement of the Oxygen Ratio

The oxygen ratio was measured under an energy resolution of 0.9 eV for each of the contact lenses according to the Samples Nos. 1~18 of the present invention and the Comparative Samples Nos. 1 and 2 by an X-ray photoelectron spectrometer ("JPS-9000MX" available from JEOL Ltd., Japan) using MgK$_\alpha$ non-monochromatic X-ray as the excitation X-ray. The results are also indicated in the following TABLE 1 and TABLE 2.

TABLE 1

| | use of lens holder | irradiation time (s) | contact angle (deg) | oxygen percent (%) | presence of cracking |
|---|---|---|---|---|---|
| Present invention | | | | | |
| Sample No. 1 | NO | 1 | 35 | 22.0 | NONE |
| Sample No. 2 | NO | 1 | 39 | — | NONE |
| Sample No. 3 | NO | 5 | <10 | 41.8 | NONE |
| Sample No. 4 | NO | 5 | <10 | — | NONE |
| Sample No. 5 | NO | 10 | <10 | 42.9 | NONE |
| Sample No. 6 | NO | 10 | <10 | — | NONE |
| Sample No. 7 | YES | 1 | 35 | 28.3 | NONE |
| Sample No. 8 | YES | 1 | 34 | — | NONE |
| Sample No. 9 | YES | 5 | <10 | 36.5 | NONE |
| Sample No. 10 | YES | 5 | <10 | — | NONE |
| Sample No. 11 | YES | 10 | <10 | 44.4 | NONE |
| Sample No. 12 | YES | 10 | <10 | — | NONE |
| Comparative Sample No. 1 | NO | 0 | 89 | 14.8 | NONE |

—: not measured

TABLE 2

| | irradiation time (s) | contact angle (deg) | Oxygen percent (%) | presence of cracking |
|---|---|---|---|---|
| Present invention | | | | |
| Sample No. 13 | 1 | 29 | 22.0 | NONE |
| Sample No. 14 | 1 | 30 | — | NONE |
| Sample No. 15 | 5 | 29 | 25.7 | NONE |
| Sample No. 16 | 5 | 29 | — | NONE |
| Sample No. 17 | 10 | 29 | 25.3 | NONE |
| Sample No. 18 | 10 | 27 | — | NONE |
| Comparative Sample No. 2 | 0 | 37 | 20.0 | NONE |

—: not measured

As is apparent from the results indicated in the above TABLE 1 and TABLE 2, the contact lenses according to the Comparative Samples Nos. 1 and 2 which were not subjected to the plasma treatment have relatively large contact angles, and therefore suffer from low wettability. In contrast, the contact lenses according to the Samples Nos. 1~12 and 13~18 of the present invention do not suffer from any cracking and have relatively small contact angles, exhibiting improved wettability. It is noted that the contact angle decreases with an increase of the plasma irradiation time.

The oxygen ratio increases with an increase with an increase of the plasma irradiation time. It is apparent from the results indicated in TABLE 1 that the contact lenses can be sufficiently irradiated with the plasma even when they are held by the lens holders.

Example 2

Sterilizing Effect

Six pieces of silicon-containing RGP contact lenses were prepared. A spore suspension (*Bacillus subtilis* IF05313) of $10^5$ cfu/mL was prepared, and 10 μL of this suspension was applied to the contact lenses at about $10^3$ cfu/lens. Then, the contact lenses were air-dried. As in the Example 1, the plasma gas was blown onto three of these six contact lenses for surface modification, to thereby provide Samples Nos. 19~21 according to the present invention. These contact lenses according to the Samples Nos. 19~21 were irradiated with the plasma under the same conditions as in Example 1, except that the irradiation time was 10 seconds in this Example 2.

One of the other three contact lenses was used as a Comparative Sample No. 3 without effecting any treatment. As for the other two contact lenses, the air without containing plasma was blown, to thereby provide Comparative Samples Nos. 4 and 5.

A plate count of the *Bacillus subtilis* remaining on each of the thus obtained Samples Nos. 19~21 of the present invention and the Comparative Samples Nos. 3~5 was measured in the following manner. After each contact lens sample was accommodated in a sterile glass vial, 2 mL of 0.1 w/v % polysorbate-added-peptone-sodium buffer was added thereto. The mixture was stirred by a vortex mixer at its maximal speed for 10 seconds. Thereafter, 0.1 mL of the solution in which the *Bacillus subtilis* was dissolved was taken out of the vial, and was plated on two soybean casein digest agar plates (SCDA plates). The agar plates were incubated in an incubator kept at 32° C. overnight. Thereafter, the number of colony was obtained for each agar plate. The average value of the numbers of colony of the two plates were calculated, to thereby obtain the plate count (cfu/lens) for each contact lens sample. The results are indicated in the following TABLE 3. There were obtained an average value of the plate counts of the Samples Nos. 19~21 of the present invention which had been subjected to the plasma treatment, and an average value of the plate counts of the Comparative Samples Nos. 4 and 5 which had been subjected to the air-blow treatment. Those average values are also indicated in the TABLE 3.

TABLE 3

|  | plate count (cfu/lens) | average value (cfu/lens) |
|---|---|---|
| Present invention |  |  |
| Sample No. 19 | 220 | 273.3 |
| Sample No. 20 | 300 |  |
| Sample No. 21 | 300 |  |
| Comparative Sample No. 3 | 460 | 460 |
| Comparative Sample No. 4 | 470 | 495 |
| Comparative Sample No. 5 | 520 |  |

As is apparent from the results indicated in the TABLE 3, the air-blow treated contact lenses according to the Comparative Samples Nos. 4 and 5 had substantially the same plate counts of the *Bacillus subtilis* as the non-treated contact lens according to the Comparative Sample No. 3. It is recognized that the *Bacillus subtilis* adhering to the contact lenses according to the Comparative Samples Nos. 4 and 5 was not substantially removed by the air blown onto these contact lens samples. In contrast, in the contact lenses according to the Samples Nos. 19~21 of the present invention, about 40% of the *Bacillus subtilis* was killed as calculated according to the following equation. Accordingly, it is to be understood that the contact lenses according to the Samples Nos. 19~21 of the present invention were effectively sterilized by the irradiation of the plasma.

kill rate of *Bacillus subtilis* (%)=(average plate count of the non-treated contact lens−average plate count of the plasma-treated contact lenses)÷average plate count of the non-treated contact lens×100=40.6

It is speculated from the results indicated in the above Example 1 that the kill rate will increase with an increase of the plasma irradiation time. Further, if the gas is introduced into the plasma generating device after the gas is in contact with hydrogen peroxide water, the sterilizing effect will increase since the formation of OH radicals and O radicals is activated.

Example 3

15 pieces of silicon-containing hydrogel soft contact lenses as the ophthalmic lens were used as the Samples Nos. 22~33 according to the present invention and the Comparative Samples Nos. 6~8. The plasma irradiator "ST-7000" available from KABUSHIKI KAISHA KEYENCE, Japan was used as the plasma generating device. Further, the following three plasma control members were prepared:

wire framework
  material: iron
  size of the opening: 12.1 mm
  diameter of the wire: 1.4 mm
planar member A
  material: polytetrafluoroethylene
  ratio of the opening: 23%
  configuration of the opening: circle
  diameter of the opening: 1.0 mm
  area of the opening: 0.8 mm²
  center-to-center distance of adjacent two openings: 2.0 mm
  thickness: 0.5 mm
planar member B
  material: aluminum
  ratio of the opening: 37%
  configuration of the opening: circle
  diameter of the opening: 3.0 mm
  area of the opening: 7.1 mm²
  center-to-center distance of the adjacent two openings: 4.8 mm
  thickness: 0.5 mm The contact lens samples were subjected to the surface modification treatment in the following manner. Each of the contact lenses was held by a flexible lens holder, and is disposed such that its optical axis is parallel to the direction in which the plasma is blown from the plasma irradiator. As the plasma control member, the wire framework described above was used for the contact lenses according to the Samples Nos. 22~24 of the present invention, the planar member A described above was used for the contact lenses according to the Samples Nos. 25~27 of the present invention, and the planar member B was used for the contact lenses according to the Samples Nos. 28~30 of the present invention. The plasma control member was interposed between each sample and the plasma generating device, as shown in FIG. 5. In this state, the front and back surfaces of each contact lens sample were exposed to one plasma blow. Each of the contact lenses according to the Samples Nos. 31~33 of the present invention were irradiated with the plasma with the planar member B as the plasma control member being fixed to the plasma irradiator by using a glass tube, as shown in FIG. 6. Described in detail, the glass tube having a diameter large enough to surround the end portion of the plasma irradiator is fixed at one of its opposite end faces to the end portion of the plasma irradiator and at the other end face to the planar member B. In this state, the front and back surfaces of each contact lens sample were exposed to one plasma blow. The contact lenses according to the Comparative Samples Nos. 6~8 were irradiated with the plasma without the wire framework and the planar members A, B being interposed between the each sample and the plasma irradiator. In this Example 3, the work distance was 10 mm.

Each contact lens sample which has been subjected to the surface modification described above was observed under a stereomicroscope at 200×(available from KABUSHIKI KAISHA NEITZ, Japan), for examining whether the contact lens sample suffers from any cracking. The results of examination are indicated in the following TABLE 4. As for the contact lens according to the Sample No. 6 of the present invention and the contact lens according to the Comparative Sample No 28, the edge portions were photographed by a differential interference microscope at 100×("OPTIPHOT-2" available from Nikon Corporation, Japan). The micrographs of the Sample No. 6 and the Comparative Sample No. 28 are shown in FIGS. 12 and 13, respectively.

TABLE 4

| | plasma control member | presence of cracking | ratio of contact lenses suffering from cracking |
|---|---|---|---|
| Comparative Sample No. 6 | — | observed | 2/3 |
| Comparative Sample No. 7 | — | observed | |
| Comparative Sample No. 8 | — | not observed | |
| Present invention | | | |
| Sample No. 22 | wire framework | not observed | 0/3 |
| Sample No. 23 | wire framework | not observed | |
| Sample No. 24 | wire framework | not observed | |
| Sample No. 25 | planar member A | not observed | 0/3 |
| Sample No. 26 | planar member A | not observed | |
| Sample No. 27 | planar member A | not observed | |
| Sample No. 28 | planar member B | not observed | 0/3 |
| Sample No. 29 | planar member B | not observed | |
| Sample No. 30 | planar member B | not observed | |
| Sample No. 31 | planar member B | not observed | 0/3 |
| Sample No. 32 | planar member B | not observed | |
| Sample No. 33 | planar member B | not observed | |

Figure 12:
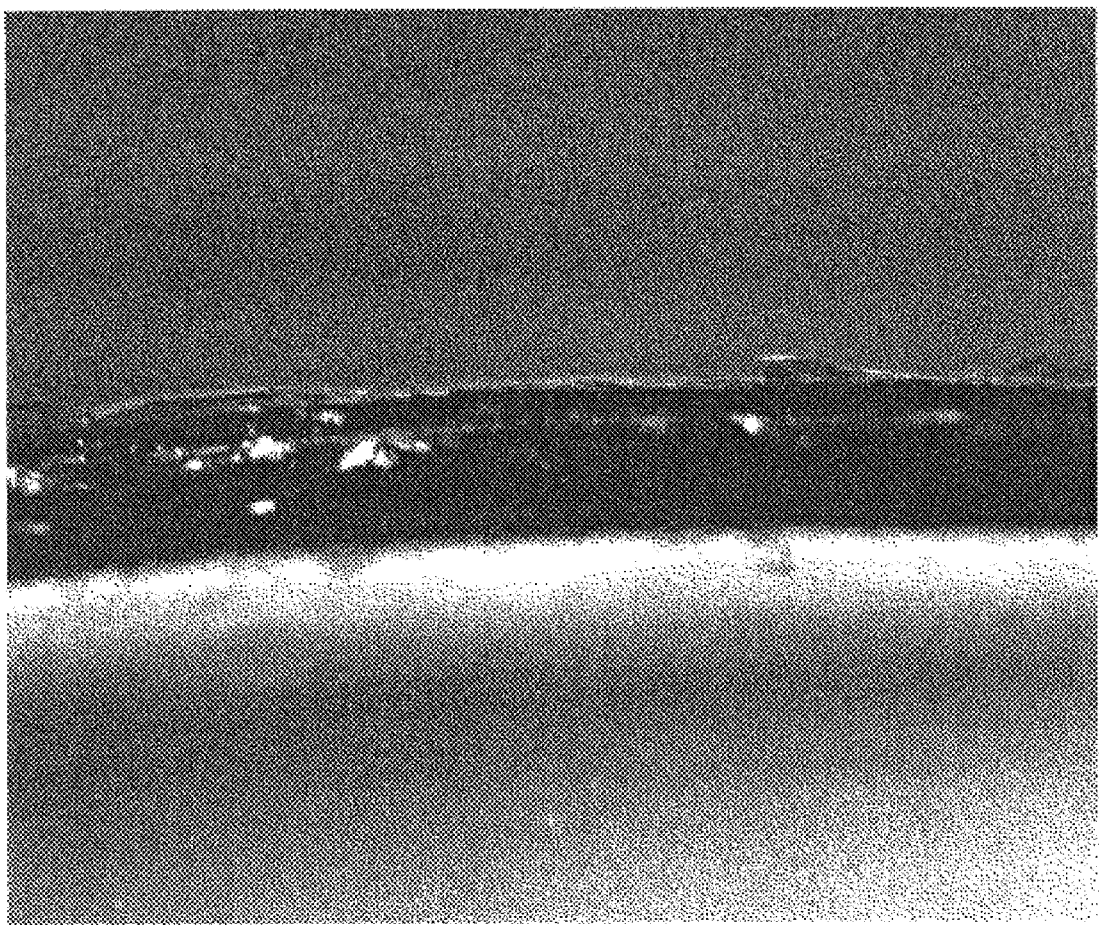
FIG. 12 is a microphotograph showing an edge portion of the contact lens according to the Comparative sample No. 6 in Example 3, which was irradiated with the plasma without the plasma control member being interposed between the plasma generating device and the sample lens.
Figure 13:
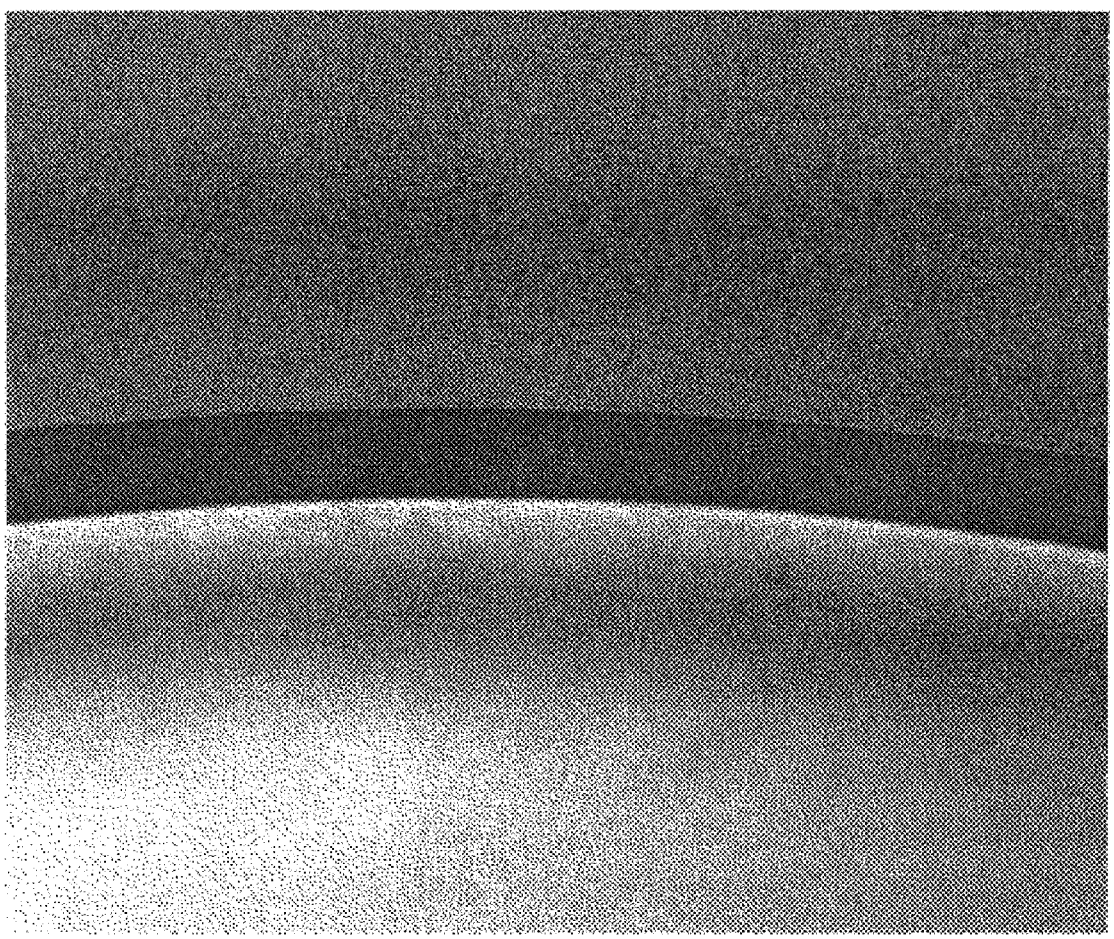
FIG. 13 is a microphotograph showing an edge portion of the contact lens according to the Sample No. 28 of the present invention in Example 3, which was irradiated with the plasma with the plasma control member being interposed between the plasma generating device and the sample lens.

As is apparent from the results indicated in the TABLE 4 and the micrographs of FIGS. 12 and 13, each of the contact lenses according to the Comparative Samples Nos. 6~8 onto which the plasma was directly blown suffered from cracking. In contrast, the contact lenses according to Samples Nos. 22~33 of the present invention did not suffer from any cracking since the plasma was blown onto these contact lenses through the openings of the plasma control member, that is, through the openings of the wire framework or the perforations of the planar member.

What is claimed is:

1. A method of modifying a surface of an ophthalmic lens, comprising the steps of:
   positioning said ophthalmic lens in a flexible lens holder;
   generating plasma at an atmospheric pressure; and
   contacting said ophthalmic lens while positioned within said flexible lens holder with said plasma to modify the surface of said ophthalmic lens to form a final ophthalmic lens product.

2. A method according to claim 1, wherein said step of contacting said ophthalmic lens with said plasma comprises a step of blowing said plasma onto said ophthalmic lens through at least one opening of a plasma control member which is spaced apart from the surface of said ophthalmic lens.

3. A method according to claim 2, wherein said plasma control member has a matrix of a multiplicity of openings.

4. A method according to claim 2, wherein said plasma control member is a network which has a matrix of a multiplicity of openings.

5. A method according to claim 2, wherein said plasma control member is a planar member which has a matrix of a multiplicity of perforations formed through a thickness thereof.

6. A method according to claim 4, wherein each of the multiplicity of openings of said network has a size of 0.3~15 mm.

7. A method according to claim 4, wherein said network is a wire framework comprising a plurality of wires, each of the plurality of wires having a diameter of 0.1~3 mm.

8. A method according to claim 5, wherein said planar member has an opening ratio of 15~70%.

9. A method according to claim 5, wherein said planar member is a sheet member having perforations formed by punching, said sheet member having a thickness in a range of 0.1~3 mm.

10. A method of modifying a surface of an ophthalmic lens, comprising the steps of:
    generating plasma at an atmospheric pressure between electrodes of a plasma generating device; and
    blowing said plasma from said plasma generating device by introducing a gas between said electrodes, so as to irradiate said ophthalmic lens located in an ambient atmosphere outside said plasma generating device with said plasma blown out from said plasma generating device to modify the surface of said ophthalmic lens.

11. A method according to claim 10, further comprising a step of interposing a plasma control member between said ophthalmic lens and said plasma generating device, and wherein said plasma is blown onto said ophthalmic lens through at least one opening of said plasma control member.

12. A method according to claim 11, wherein said plasma control member has a matrix of a multiplicity of openings.

13. A method according to claim 11, wherein said plasma control member is a network which has a matrix of a multiplicity of openings.

14. A method according to claim 11, wherein said plasma control member is a planar member which has a matrix of perforations formed through a thickness thereof.

15. A method according to claim 13, wherein each of the multiplicity of openings of said network has a size of 0.3~15 mm.

16. A method according to claim 13, wherein said network is a wire framework comprising a plurality of wires, each of the plurality of wires having a diameter of 0.1~3 mm.

17. A method according to claim 14, wherein said planar member has an opening ratio of 15~70%.

18. A method according to claim 14, wherein said planar member is a sheet member having perforations formed by punching, said sheet member having a thickness in a range of 0.1~3 mm.

19. A method according to claim 10, wherein said step of blowing said plasma is effected on at least one ophthalmic lens while said at least one ophthalmic lens is moved relative to said plasma generating device by a conveyor.

20. A method according to claim 10, wherein said step of blowing said plasma is effected while said ophthalmic lens is held by a flexible lens holder.

21. A method according to claim 10, wherein said plasma is blown out from said plasma generating device in a direction which is perpendicular to an optical axis of said ophthalmic lens, so that said plasma flows laterally onto said ophthalmic lens.

22. A method according to claim 10, wherein said plasma is blown onto one of opposite surfaces of said ophthalmic lens in a direction parallel to an optical axis of said ophthalmic lens.

23. A method according to claim 10, wherein said plasma is blown onto opposite surfaces of said ophthalmic lens in opposite directions which are parallel to said optical axis of said ophthalmic lens.

24. A method according to claim 10, wherein said gas introduced between said electrodes of said plasma generating device is selected from the group consisting of nitrogen, oxygen, helium, neon, argon, and mixtures thereof.

25. A method according to claim 10, wherein said gas introduced between said electrodes of said plasma generating device is atmospheric air.

26. A method according to claim 10, wherein said ophthalmic lens is irradiated with said plasma for a time period in a range between 0.01 second and 180 seconds.

27. A method according to claim 10, wherein said ophthalmic lens is a contact lens.

28. A method according to claim 10, wherein said ophthalmic lens is formed in a mold cavity defined by and between two molds of a mold assembly, and said plasma is blown on one of opposite surfaces of said ophthalmic lens while it is held by one of said two molds which have been separated away from each other, so that said one of opposite surfaces of said ophthalmic lens which has been removed from the other of said two molds is irradiated with said plasma.

29. A method according to claim 10, wherein said plasma is generated by a glow discharge.

30. A method according to claim 10, wherein the surface of said ophthalmic lens is sterilized by irradiation of said plasma.

31. A method according to claim 10, wherein said gas is introduced between said electrodes of said plasma generating device after said gas is in contact with hydrogen peroxide water.

* * * * *

UNITED STATES PATENT AND TRADEMARK OFFICE
CERTIFICATE OF CORRECTION

PATENT NO.   : 6,610,350 B2
DATED        : August 26, 2003
INVENTOR(S)  : Hiroaki Suzuki, Yuuji Gotou and Kazuhiko Nakada It is certified that error appears in the above-identified patent and that said Letters Patent is hereby corrected as shown below:

<u>Title page,</u>
Item [56], FOREIGN PATENT DOCUMENTS, please change "JP A-8-456920" to -- JP A-8-156920 --.

Signed and Sealed this

Twenty-third Day of December, 2003

JAMES E. ROGAN
*Director of the United States Patent and Trademark Office*